US009888956B2

(12) United States Patent
Model et al.

(10) Patent No.: US 9,888,956 B2
(45) Date of Patent: Feb. 13, 2018

(54) INTEGRATED PUMP AND GENERATOR DEVICE AND METHOD OF USE

(71) Applicant: AngioDynamics, Inc., Latham, NY (US)

(72) Inventors: Jeffrey Model, Cambridge, MA (US); Robert Rioux, Ashland, MA (US)

(*) Notice: Subject to any disclaimer, the term of this patent is extended or adjusted under 35 U.S.C. 154(b) by 448 days.

(21) Appl. No.: 14/160,881

(22) Filed: Jan. 22, 2014

(65) Prior Publication Data

US 2014/0207133 A1    Jul. 24, 2014

Related U.S. Application Data

(60) Provisional application No. 61/755,426, filed on Jan. 22, 2013, provisional application No. 61/771,574, filed on Mar. 1, 2013, provisional application No. 61/824,843, filed on May 17, 2013.

(51) Int. Cl.
| | |
|---|---|
| *A61B 18/12* | (2006.01) |
| *A61B 18/18* | (2006.01) |
| *A61B 17/00* | (2006.01) |
| *A61B 18/00* | (2006.01) |

(52) U.S. Cl.
CPC ...... *A61B 18/1206* (2013.01); *A61B 18/1815* (2013.01); *A61B 2017/0023* (2013.01); *A61B 2018/00029* (2013.01); *A61B 2018/00577* (2013.01); *A61B 2018/00613* (2013.01)

(58) Field of Classification Search
CPC .. A61B 2017/0023; A61B 2018/00011; A61B 2018/00023; A61B 2018/00029; A61B 2018/00172; A61B 2018/00178; A61B 2018/00613

USPC .................................... 606/41; 607/99, 113
See application file for complete search history.

(56) References Cited

U.S. PATENT DOCUMENTS

| | | | |
|---|---|---|---|
| 4,267,047 A | 5/1981 | Henne et al. | |
| 4,447,235 A | 5/1984 | Clarke | |
| 4,489,535 A | 12/1984 | Veltman | |
| 4,672,969 A | 6/1987 | Dew | |
| 4,676,258 A | 6/1987 | Inokuchi et al. | |
| 4,716,896 A | 1/1988 | Ackerman | |
| 4,756,838 A | 7/1988 | Veltman | |
| 4,810,963 A | 3/1989 | Blake-Coleman et al. | |
| 4,889,634 A | 12/1989 | El-Rashidy | |

(Continued)

FOREIGN PATENT DOCUMENTS

| | | |
|---|---|---|
| AU | 2003227960 A1 | 12/2012 |
| CA | 2445392 A1 | 11/2002 |

(Continued)

OTHER PUBLICATIONS

Pinero, et al, Apoptotic and necrotic cell death are both induced by electroporation in HL60 human promyeloid leukaemia cells, Apoptosis, 1997, 2, pp. 330-336.

(Continued)

*Primary Examiner* — Thomas Giuliani
(74) *Attorney, Agent, or Firm* — Zachary F. Madonna, Esq.

(57) ABSTRACT

The present disclosure relates to devices and methods for the cooling of ablation technology used to treat tissue. The devices and methods disclosed herein utilize a multiple use generator assembly which includes an integrated cooling system, and a disposable, single-use subassembly which includes a disposable pump head and ablation device.

10 Claims, 9 Drawing Sheets

(56) References Cited

U.S. PATENT DOCUMENTS

| | | |
|---|---|---|
| 4,891,483 A | 1/1990 | Kikuchi et al. |
| 4,907,601 A | 3/1990 | Frick |
| 4,946,793 A | 8/1990 | Marshall, III |
| 5,098,843 A | 3/1992 | Calvin |
| 5,173,158 A | 12/1992 | Schmukler |
| 5,283,194 A | 2/1994 | Schmukler |
| 5,328,451 A | 7/1994 | Davis et al. |
| 5,334,167 A | 8/1994 | Cocanower |
| 5,439,440 A | 8/1995 | Hofmann |
| 5,462,521 A | 10/1995 | Brucker et al. |
| 5,484,401 A | 1/1996 | Rodriguez et al. |
| 5,562,720 A | 10/1996 | Stern et al. |
| 5,582,588 A | 12/1996 | Sakurai et al. |
| 5,586,982 A | 12/1996 | Abela |
| 5,588,424 A | 12/1996 | Insler et al. |
| 5,643,197 A | 7/1997 | Brucker et al. |
| 5,645,855 A | 7/1997 | Lorenz |
| 5,697,905 A | 12/1997 | d'Ambrosio |
| 5,720,921 A | 2/1998 | Meserol |
| 5,735,847 A | 4/1998 | Gough et al. |
| 5,807,395 A | 9/1998 | Mulier et al. |
| 5,810,804 A | 9/1998 | Gough et al. |
| 5,836,897 A | 11/1998 | Sakurai et al. |
| 5,968,006 A | 10/1999 | Hofmann |
| 5,983,131 A | 11/1999 | Weaver et al. |
| 6,027,502 A | 2/2000 | Desai |
| 6,043,066 A | 3/2000 | Mangano et al. |
| 6,059,780 A | 5/2000 | Gough et al. |
| 6,066,134 A | 5/2000 | Eggers et al. |
| 6,074,389 A | 6/2000 | Levine et al. |
| 6,090,105 A | 7/2000 | Zepeda et al. |
| 6,090,106 A | 7/2000 | Goble et al. |
| 6,102,885 A | 8/2000 | Bass |
| 6,116,330 A | 9/2000 | Salyer |
| 6,132,419 A | 10/2000 | Hofmann |
| 6,134,476 A | 10/2000 | Arndt et al. |
| 6,150,148 A | 11/2000 | Nanda et al. |
| 6,258,100 B1 | 7/2001 | Alferness et al. |
| 6,280,441 B1 | 8/2001 | Ryan |
| 6,328,735 B1 | 12/2001 | Curley et al. |
| 6,347,247 B1 | 2/2002 | Dev et al. |
| 6,436,072 B1 | 8/2002 | Kullas et al. |
| 6,463,331 B1 | 10/2002 | Edwards |
| 6,488,673 B1 | 12/2002 | Laufer et al. |
| 6,488,680 B1 | 12/2002 | Francischelli et al. |
| 6,500,173 B2 | 12/2002 | Underwood et al. |
| 6,506,189 B1 | 1/2003 | Rittman, III et al. |
| 6,537,976 B1 | 3/2003 | Gupta |
| 6,575,969 B1 | 6/2003 | Rittman, III et al. |
| 6,613,211 B1 | 9/2003 | McCormick et al. |
| 6,627,421 B1 | 9/2003 | Unger et al. |
| 6,638,253 B2 | 10/2003 | Breznock |
| 6,653,091 B1 | 11/2003 | Dunn et al. |
| 6,666,858 B2 | 12/2003 | Lafontaine |
| 6,673,070 B2 | 1/2004 | Edwards et al. |
| 6,682,501 B1 | 1/2004 | Nelson et al. |
| 6,694,979 B2 | 2/2004 | Deem et al. |
| 6,697,670 B2 | 2/2004 | Chomenky et al. |
| 6,712,811 B2 | 3/2004 | Underwood et al. |
| 6,753,171 B2 | 6/2004 | Karube et al. |
| 6,770,070 B1 | 8/2004 | Balbierz |
| 6,795,728 B2 | 9/2004 | Chornenky et al. |
| 6,837,886 B2 | 1/2005 | Collins et al. |
| 6,847,848 B2 | 1/2005 | Sterzer et al. |
| 6,865,416 B2 | 3/2005 | Dev et al. |
| 6,869,430 B2 | 3/2005 | Balbierz et al. |
| 6,962,587 B2 | 11/2005 | Johnson et al. |
| 6,972,014 B2 | 12/2005 | Eum et al. |
| 6,994,706 B2 | 2/2006 | Chornenky et al. |
| 7,063,698 B2 | 6/2006 | Whayne et al. |
| 7,100,616 B2 | 9/2006 | Springmeyer |
| 7,162,303 B2 | 1/2007 | Levin et al. |
| 7,169,107 B2 | 1/2007 | Jersey-Willuhn et al. |
| 7,211,083 B2 | 5/2007 | Chornenky et al. |
| 7,232,437 B2 | 6/2007 | Berman et al. |
| 7,267,676 B2 | 9/2007 | Chornenky et al. |
| 7,344,533 B2 | 3/2008 | Pearson et al. |
| 7,419,487 B2 | 9/2008 | Johnson et al. |
| 7,437,194 B2 | 10/2008 | Skwarek et al. |
| 7,476,203 B2 | 1/2009 | DeVore et al. |
| 7,488,292 B2 | 2/2009 | Adachi |
| 7,544,301 B2 | 6/2009 | Shah et al. |
| 7,553,309 B2 | 6/2009 | Buysse et al. |
| 7,571,729 B2 | 8/2009 | Saadat et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,699,842 B2 | 4/2010 | Buysse et al. |
| 7,717,948 B2 | 5/2010 | Demarais et al. |
| 7,763,018 B2 | 7/2010 | DeCarlo et al. |
| 7,765,010 B2 | 7/2010 | Chornenky et al. |
| 7,771,401 B2 | 8/2010 | Hekmat et al. |
| 7,824,870 B2 | 11/2010 | Kovalcheck et al. |
| 7,853,333 B2 | 12/2010 | Demarais |
| 7,879,031 B2 | 2/2011 | Peterson |
| 7,937,143 B2 | 5/2011 | Demarais et al. |
| 7,951,582 B2 | 5/2011 | Gazit et al. |
| RE42,835 E | 10/2011 | Chornenky et al. |
| 8,052,604 B2 | 11/2011 | Lau et al. |
| 8,059,059 B2 | 11/2011 | Bonn |
| 8,062,290 B2 | 11/2011 | Buysse et al. |
| RE43,009 E | 12/2011 | Chornenky et al. |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,182,477 B2 | 5/2012 | Orszulak et al. |
| 8,187,269 B2 | 5/2012 | Shadduck et al. |
| 8,187,270 B2 | 5/2012 | Auth et al. |
| 8,221,411 B2 | 7/2012 | Francischelli et al. |
| 8,231,603 B2 | 7/2012 | Hobbs et al. |
| 8,252,057 B2 | 8/2012 | Fox |
| 8,292,880 B2 | 10/2012 | Prakash et al. |
| 8,346,370 B2 | 1/2013 | Haley et al. |
| 8,347,891 B2 | 1/2013 | Demarais et al. |
| 2001/0047167 A1 | 11/2001 | Heggeness |
| 2002/0052601 A1 | 5/2002 | Goldberg et al. |
| 2002/0077627 A1 | 6/2002 | Johnson et al. |
| 2002/0077676 A1 | 6/2002 | Schroeppel et al. |
| 2002/0082543 A1 | 6/2002 | Park et al. |
| 2002/0095197 A1 | 7/2002 | Lardo et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0193831 A1 | 12/2002 | Smith |
| 2003/0009110 A1 | 1/2003 | Tu et al. |
| 2003/0014047 A1 | 1/2003 | Woloszko et al. |
| 2003/0055220 A1 | 3/2003 | Legrain |
| 2003/0059945 A1 | 3/2003 | Dzekunov et al. |
| 2003/0060856 A1 | 3/2003 | Chornenky et al. |
| 2003/0088189 A1 | 5/2003 | Tu et al. |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0149451 A1 | 8/2003 | Chomenky et al. |
| 2003/0159700 A1 | 8/2003 | Laufer et al. |
| 2003/0170898 A1 | 9/2003 | Gundersen et al. |
| 2003/0199050 A1 | 10/2003 | Mangano et al. |
| 2003/0212394 A1 | 11/2003 | Pearson et al. |
| 2003/0225360 A1 | 12/2003 | Eppstein et al. |
| 2004/0059328 A1 | 3/2004 | Daniel et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0146877 A1 | 7/2004 | Diss et al. |
| 2004/0153057 A1 | 8/2004 | Davison |
| 2004/0200484 A1 | 10/2004 | Springmeyer |
| 2004/0204679 A1 | 10/2004 | Visconti et al. |
| 2004/0243107 A1 | 12/2004 | Macoviak et al. |

(56) References Cited

U.S. PATENT DOCUMENTS

| | | | |
|---|---|---|---|
| 2004/0267340 A1* | 12/2004 | Cioanta | A61F 7/123 607/105 |
| 2005/0010259 A1 | 1/2005 | Gerber | |
| 2005/0013870 A1 | 1/2005 | Freyman et al. | |
| 2005/0015081 A1 | 1/2005 | Turovskiy et al. | |
| 2005/0020965 A1 | 1/2005 | Rioux et al. | |
| 2005/0033276 A1 | 2/2005 | Adachi | |
| 2005/0043726 A1 | 2/2005 | McHale et al. | |
| 2005/0096709 A1 | 5/2005 | Skwarek et al. | |
| 2005/0143817 A1 | 6/2005 | Hunter et al. | |
| 2005/0165393 A1 | 7/2005 | Eppstein | |
| 2005/0228459 A1 | 10/2005 | Levin et al. | |
| 2005/0228460 A1 | 10/2005 | Levin et al. | |
| 2005/0234523 A1 | 10/2005 | Levin et al. | |
| 2005/0261672 A1 | 11/2005 | Deem et al. | |
| 2005/0267407 A1 | 12/2005 | Goldman | |
| 2005/0288730 A1 | 12/2005 | Deem et al. | |
| 2006/0020347 A1 | 1/2006 | Barrett et al. | |
| 2006/0025821 A1 | 2/2006 | Gelfand et al. | |
| 2006/0030810 A1 | 2/2006 | Mandrusov et al. | |
| 2006/0079883 A1 | 4/2006 | Elmouelhi et al. | |
| 2006/0106379 A1 | 5/2006 | O'Brien et al. | |
| 2006/0122673 A1* | 6/2006 | Callister | A61F 7/12 607/105 |
| 2006/0142801 A1 | 6/2006 | Demarais et al. | |
| 2006/0149123 A1 | 7/2006 | Vidlund et al. | |
| 2006/0182684 A1 | 8/2006 | Beliveau | |
| 2006/0206150 A1 | 9/2006 | Demarais et al. | |
| 2006/0212076 A1 | 9/2006 | Demarais et al. | |
| 2006/0212078 A1 | 9/2006 | Demarais et al. | |
| 2006/0217703 A1 | 9/2006 | Chornenky et al. | |
| 2006/0224188 A1 | 10/2006 | Libbus et al. | |
| 2006/0235474 A1 | 10/2006 | Demarais | |
| 2006/0271111 A1 | 11/2006 | Demarais et al. | |
| 2006/0293734 A1* | 12/2006 | Scott | A61F 7/12 607/105 |
| 2007/0021803 A1 | 1/2007 | Deem et al. | |
| 2007/0025919 A1 | 2/2007 | Deem et al. | |
| 2007/0055142 A1 | 3/2007 | Webler | |
| 2007/0060989 A1 | 3/2007 | Deem et al. | |
| 2007/0066957 A1 | 3/2007 | Demarais et al. | |
| 2007/0078391 A1 | 4/2007 | Wortley et al. | |
| 2007/0078453 A1 | 4/2007 | Johnson et al. | |
| 2007/0083239 A1 | 4/2007 | Demarais et al. | |
| 2007/0129711 A1 | 6/2007 | Altshuler et al. | |
| 2007/0137567 A1 | 6/2007 | Shimizu et al. | |
| 2007/0156129 A1 | 7/2007 | Kovalcheck | |
| 2007/0156135 A1 | 7/2007 | Rubinsky et al. | |
| 2007/0156136 A1 | 7/2007 | Godara et al. | |
| 2007/0173899 A1 | 7/2007 | Levin et al. | |
| 2007/0191889 A1 | 8/2007 | Lang | |
| 2007/0203549 A1 | 8/2007 | Demarais et al. | |
| 2007/0203551 A1 | 8/2007 | Cronin et al. | |
| 2007/0295336 A1 | 12/2007 | Nelson et al. | |
| 2007/0295337 A1 | 12/2007 | Nelson et al. | |
| 2008/0015628 A1 | 1/2008 | Dubrul et al. | |
| 2008/0071262 A1 | 3/2008 | Azure | |
| 2008/0097422 A1 | 4/2008 | Edwards et al. | |
| 2008/0132826 A1 | 6/2008 | Shadduck et al. | |
| 2008/0146934 A1 | 6/2008 | Czygan et al. | |
| 2008/0213331 A1 | 9/2008 | Gelfand et al. | |
| 2008/0236593 A1 | 10/2008 | Nelson et al. | |
| 2008/0275436 A1 | 11/2008 | Cronin et al. | |
| 2008/0279995 A1 | 11/2008 | Schultheiss et al. | |
| 2008/0283065 A1 | 11/2008 | Chang et al. | |
| 2008/0294155 A1 | 11/2008 | Cronin | |
| 2009/0018206 A1 | 1/2009 | Barkan et al. | |
| 2009/0018565 A1 | 1/2009 | To et al. | |
| 2009/0018566 A1 | 1/2009 | Escudero et al. | |
| 2009/0018567 A1 | 1/2009 | Escudero et al. | |
| 2009/0024075 A1 | 1/2009 | Schroeppel et al. | |
| 2009/0024085 A1 | 1/2009 | To et al. | |
| 2009/0029407 A1 | 1/2009 | Gazit et al. | |
| 2009/0036773 A1 | 2/2009 | Lau et al. | |
| 2009/0081272 A1 | 3/2009 | Clarke et al. | |
| 2009/0105703 A1 | 4/2009 | Shadduck | |
| 2009/0114226 A1 | 5/2009 | Deem et al. | |
| 2009/0118725 A1 | 5/2009 | Auth et al. | |
| 2009/0118729 A1 | 5/2009 | Auth et al. | |
| 2009/0143705 A1 | 6/2009 | Danek et al. | |
| 2009/0157166 A1 | 6/2009 | Singhal et al. | |
| 2009/0163904 A1 | 6/2009 | Miller et al. | |
| 2009/0177111 A1 | 7/2009 | Miller et al. | |
| 2009/0192508 A1 | 7/2009 | Laufer et al. | |
| 2009/0198231 A1 | 8/2009 | Esser et al. | |
| 2009/0221939 A1 | 9/2009 | Demarais et al. | |
| 2009/0269317 A1 | 10/2009 | Davalos | |
| 2009/0275827 A1 | 11/2009 | Aiken et al. | |
| 2009/0295674 A1 | 12/2009 | Bonn | |
| 2010/0004623 A1 | 1/2010 | Hamilton, Jr. et al. | |
| 2010/0016783 A1 | 1/2010 | Bourke, Jr. et al. | |
| 2010/0023004 A1 | 1/2010 | Francischelli et al. | |
| 2010/0030211 A1 | 2/2010 | Davalos et al. | |
| 2010/0057074 A1 | 3/2010 | Roman et al. | |
| 2010/0069921 A1 | 3/2010 | Miller et al. | |
| 2010/0082022 A1 | 4/2010 | Haley et al. | |
| 2010/0106047 A1 | 4/2010 | Sarfaty et al. | |
| 2010/0121173 A1 | 5/2010 | Sarfaty et al. | |
| 2010/0168735 A1 | 7/2010 | Deno et al. | |
| 2010/0174282 A1 | 7/2010 | Demarais et al. | |
| 2010/0179530 A1 | 7/2010 | Long et al. | |
| 2010/0191112 A1 | 7/2010 | Demarais et al. | |
| 2010/0204638 A1 | 8/2010 | Hobbs et al. | |
| 2010/0256630 A1 | 10/2010 | Hamilton, Jr. et al. | |
| 2010/0262067 A1 | 10/2010 | Chomenky et al. | |
| 2010/0331758 A1 | 12/2010 | Davalos et al. | |
| 2010/0331911 A1 | 12/2010 | Kovalcheck et al. | |
| 2011/0021970 A1 | 1/2011 | Vo-Dinh et al. | |
| 2011/0064671 A1 | 3/2011 | Bynoe | |
| 2011/0082414 A1 | 4/2011 | Wallace | |
| 2011/0098695 A1 | 4/2011 | Brannan | |
| 2011/0112434 A1 | 5/2011 | Ghabrial et al. | |
| 2011/0112531 A1 | 5/2011 | Landis et al. | |
| 2011/0118721 A1 | 5/2011 | Brannan | |
| 2011/0118727 A1 | 5/2011 | Fish et al. | |
| 2011/0144524 A1 | 6/2011 | Fish et al. | |
| 2011/0144657 A1 | 6/2011 | Fish et al. | |
| 2011/0152906 A1 | 6/2011 | Escudero et al. | |
| 2011/0152907 A1 | 6/2011 | Escudero et al. | |
| 2011/0178570 A1 | 7/2011 | Demarais | |
| 2011/0207758 A1 | 8/2011 | Sobotka et al. | |
| 2011/0208096 A1 | 8/2011 | Demarais et al. | |
| 2011/0208180 A1 | 8/2011 | Brannan | |
| 2011/0217730 A1 | 9/2011 | Gazit et al. | |
| 2011/0282354 A1 | 11/2011 | Schulte et al. | |
| 2012/0034131 A1 | 2/2012 | Rubinsky et al. | |
| 2012/0059255 A1 | 3/2012 | Paul et al. | |
| 2012/0085649 A1 | 4/2012 | Sano et al. | |
| 2012/0130289 A1 | 5/2012 | Demarais et al. | |
| 2012/0150172 A1 | 6/2012 | Ortiz et al. | |
| 2012/0226271 A1 | 9/2012 | Callas et al. | |
| 2012/0265186 A1 | 10/2012 | Burger et al. | |
| 2012/0310237 A1 | 12/2012 | Swanson | |

FOREIGN PATENT DOCUMENTS

| | | |
|---|---|---|
| CA | 2487284 A1 | 12/2003 |
| CA | 2751462 A1 | 11/2010 |
| CN | 1525839 A | 9/2004 |
| EP | 0378132 A2 | 7/1990 |
| EP | 0528891 A1 | 3/1993 |
| EP | 1011495 A1 | 6/2000 |
| EP | 1406685 A1 | 4/2004 |
| EP | 1462065 A2 | 9/2004 |
| EP | 1506039 A1 | 2/2005 |
| EP | 2008604 A2 | 2/2005 |
| EP | 2286754 | 2/2005 |
| EP | 2299540 | 2/2005 |
| EP | 2381829 A1 | 11/2011 |
| GB | 2415630 A | 1/2006 |
| GB | 2457299 A | 8/2009 |
| JP | 2004525726 A | 8/2004 |
| JP | 4252316 B2 | 9/2005 |
| JP | 2005526579 A | 9/2005 |

(56) References Cited

FOREIGN PATENT DOCUMENTS

| | | |
|---|---|---|
| JP | 2011511538 | 9/2005 |
| WO | WO9634571 A1 | 11/1996 |
| WO | WO9639531 A1 | 12/1996 |
| WO | WO9810745 A1 | 3/1998 |
| WO | WO0020554 A1 | 4/2000 |
| WO | WO0170114 A1 | 9/2001 |
| WO | WO02078527 A2 | 9/2001 |
| WO | WO02089686 A1 | 9/2001 |
| WO | WO02100459 A2 | 12/2002 |
| WO | WO03047684 A2 | 6/2003 |
| WO | WO03099382 A1 | 12/2003 |
| WO | WO2004037341 A2 | 5/2004 |
| WO | WO2006002943 A1 | 1/2006 |
| WO | WO2007137303 A2 | 11/2007 |
| WO | WO2009134876 A1 | 11/2009 |
| WO | WO2009135070 A1 | 11/2009 |
| WO | WO2010132472 A1 | 11/2010 |
| WO | WO2010151277 A1 | 12/2010 |
| WO | WO2011042720 | 12/2010 |
| WO | WO2011062653 A1 | 5/2011 |
| WO | WO2011072221 A1 | 6/2011 |
| WO | WO2011135294 A1 | 11/2011 |
| WO | WO2012006533 A1 | 1/2012 |
| WO | WO2012063266 A2 | 5/2012 |
| WO | WO2012071526 A2 | 5/2012 |

OTHER PUBLICATIONS

Duraiswami, et al, Efficient 2D and3D electrical impedance tomography using dual reciprocity boundary element techniques, Engineering Analysis with Boundary Elements, 1998, 22, pp. 13-31.

Eppich, et al, Pulsed electric fields for seletion of hematopoietic cells and depletion of tumor cell contaminants, Nature America, Aug. 2000, vol. 18, pp. 882-887.

Mir, Therapeutic perspectives of in vivo cell electropermeabilization, Bioelectrochemistry, 2000, 53, pp. 1-10.

Miklavcic, et al, A validated model of in vivo electric field distribution in tissues for electrochemotherapy and for DNA electrotransfer for gene therapy, Biochimica et Biophysica Acta, 2000, 1523, pp. 73-83.

O'Brien, et al, Investigation of the Alamar Blue (resarzurin) fluorescent dye for the assessment of mammalian cell cytotoxicity, Eur J Biochem, 2000, 267, pp. 5421-5426.

Carson, et al, Improving patient satisfaction, BPH management strategies, Supplement to Urology Times, May 2001, Vo. 29, Suppl. 1, pp. 1-22.

Hall, et al, Nanosecond pulsed electric fields induce apoptosis in p53-wildtype and p53-null HCT116 colon carcinoma cells, Apoptosis, May 23, 2007, 12, pp. 1721-1731.

Esser, et al, Towards solid tumor treatment by irreversible electroporation: Intrinsic redistribution of fields and currents in tissue, Technology in Cancer Research and Treatment, Aug. 2007, vol. 6, No. 4, pp. 261-273.

Rubinsky, Irreversible electroporation in medicine, Technology in Cancer Research and Treatment, Aug. 2007, vol. 8, No. 4, pp. 255-259.

Fischbach, et al, Engineering tumors with 3D scaffolds, Nature Methods, Sep 2, 2007, vol. 4, No. 10, pp. 855-860.

Al-Sakere, et al, Tumor ablation with irreversible electroporation, PLOS One, Nov. 7, 2007, Iss. 11, e1135, pp. 1-8.

Seidler, et al, A Cre-IoxP-based mouse model for conditional somatic gene expression and knockdown in vivo by using avian retroviral vectors, PNAS, Jul. 22, 2008, vol. 105, No. 29, pp. 10137-10142.

Ivorra, et al, In vivo electrical conductivity measurements during and after tumor electroporation: conductivity changes reflect the treatment,Phys. Med. Biol., Sep. 17, 2009, 54, pp. 5949-5963.

Naslund, Transurethral Needle Ablation of the Prostate, Urology 1997, pp. 167-172.

Rubinskey, Cryosurgery, Annu. Rev. Biomed. Eng. 2000, 02: pp. 157-187.

Naslund, et al, Cost-effectiveness of Minimally Invasive Treatments and Transurethral Resection in Benign Prostatic Hyperplasia, AUA National Meeting, 2001, pp. 1213.

Gervais, et al, Society of Interventional Radiology Position Statement on Percutaneous RF Ablation for the Treatment of Liver Tumors, 2009, J Vasc Interv Radiol, pp. 3-8.

DeBenedectis, et al, Utility of Iodinated Contrast Medium in Hydrodissection Fluid when Performing Renal Tumor Ablation, J Vasc Interv Radiol 2010, pp. 745-747.

Rajagopal, Rockson, Coronary restenosis: A review of mechanisms and management, The American Journal of Medicine, Nov. 2003, vol. 115, pp. 547-553.

Sersa, et al, Tumor blood flow modifying effects of electrochemotherapy: a potential vascular targeted mechanism, Radiol Oncol, 2003, 37, 1, pp. 43-48.

Machado-Aranda, et al, Gene transfer of the Na+, K+K-ATPase B1 subunit using electroporation increases lung liquid clearance, American Journal of Respiratory and Critical Care Medicine, 2004, vol. 171, pp. 204-211.

Marty, et al, Electrochemotherapy—An easy, highly effective and safe treatment of cutaneous and subcutaneous metastases: Results of ESOPE (European Standard Operating Procedures of Electrochemotherapy) study, EJC Supplements, 2006, 4, pp. 3-13.

Demirbas, Thermal energy storage and phase change materials: An overview, Energy Sources, Part B, 2006, 1, pp. 85-95.

Neumann, Rosenheck, Permeability changes induced by electric impulses in vesicular membranes, J. Membrane Biol., 1972, 10, pp. 279-290.

Crowley, Electrical breakdown of bimolecular lipid membranes as an electromechanical instability, Biophysical Journal, 1973, vol. 13, 711-724.

Zimmermann, et al, Dielectric breakdown of cell membranes, Biophysical Journal, 1974, vol. 14, pp. 881-899.

Organ, Electrophysiologic principles of radiofrequency lesion making, Appl. Neurophysiol., 1976, 39, pp. 69-76.

Kinsoita, Jr., Tsong, Formation and resealing of pores of controlled sizes in human erythrocyte membrane, Aug. 1977, vol. 268, pp. 438-441.

Kinosita, Jr., Tsong, Voltage-induced pore formation and hemolysis of human erythrocytes, Biochimica et Biophysica Acta, 1977, pp. 227-242.

Baker, Knight, Calcium-dependent exocytosis in bovine adrenal medullary cells with leaky plasma membranes, Nature, Dec. 1978, vol. 276, pp. 620-622.

Gauger, Bentrup, A study of dielectric membrane breakdown in the Fucus egg, J. Membrane Biol., 1979, 48, pp. 249-264.

Erez, Shitzer, Controlled destruction and temperature distributions in biological tissues subjected to monactive electrocoagulation, Transactions of theASME, Feb. 1980, vol. 102, pp. 42-49.

Neumann, et al, Gene transfer into mouse lyoma cells by electroporation in high electric fields, The EMBO Journal, 1982, vol. 1, No. 7, pp. 841-845.

Seibert, et al, Clonal variation of MCF-7 breast cancer cells in vitro and in athymic nude mice, Cancer Research, May 1983, 43, pp. 2223-2239.

Brown, Phototherapy of tumors, World J. Surg., 1983, 7, 700-709.

Onik, et al, Ultraonic characteristics of frozen liver, Cryobiology, 1984, 21, pp. 321-328.

Gilbert, et al, The use of ultrsound imaging for monitoring cryosurgery, IEEE Frontiers of Engineering and computing in Health Care, 1984, pp. 107-111.

Onik, et al, Sonographic monitoring of hepatic cryosurgery in an experimental animal model, AJR, May 1985, 144, pp. 1043-1047.

Griffiths, The importance of phase measurement in e lectrical impedance tomography, Phys. Med. Biol., Nov. 1987, vol. 32, No. 11, pp. 1435-1444.

Okino, Mohri, Effects of high-voltage electrical impulse and an anticancer drug on in vivo growing tumors, Jpn. J. Cancer Res., Dec. 1987, 78, pp. 1319-1321.

(56) References Cited

OTHER PUBLICATIONS

Kinosita, Jr. et al, Electroporation of cell membrane visualized under a pulsed-laser fluorescence microscope, Biophys. J., Jun. 1988, vol. 53, pp. 1015-1019.

Amasha, et al, Quantitative assessment of impedance tomography for temperature measurements in microwave hyperthermia, Clin. Phys. Physiol. Meas., 1988, vol. 9, Suppl. A, pp. 49-53.

Asmai, et al, Dielectric properties of mouse lymphocytes and erythrocytes, Biochimica et Biophysica Acta, 1989, 1010, pp. 49-55.

Griffiths, Zhang, A dual-frequency electrical impedance tomography system, Phys. Med. Biol., 1989, vol. 34, No. 10, pp. 1465-1476.

Rowland, et al, Transvenous ablation of atrioventricular conduction with a low energy power source, Br Heart J, 1989, 62, pp. 361-366.

Marsazalek, et al, Schwan equation and transmembrane potential induced by alternating electric field, Biophysical Journal, Oct. 1990, vol. 58, pp. 1053-1058.

Tekle, et al, Electroporation by using bipolar oscillating electric field: An improved method for DNA transfection of NIH 3T3 cells, Biochemistry, May 1991, vol. 88, pp. 4230-4234.

Mir, et al, Electrochemotherapy potentiation of antitumour effect of bleomycin by local electric pulses, Eur. J. Cancer, 1991, vol. 27, No. 1, pp. 68-72.

Mir, et al, Electrochemotherapy, a novel antitumor treatment: first clinical trial, Cancerology, 1991, 313, pp. 613-618.

Narayan, Dahiya, Establishment and characterization of a human primay prostatic adenocarcinoma cell line (ND-1_, The Journal of Urology, Nov. 1992, vol. 148, pp. 1600-1604.

Griffiths, et al, Measurement of pharyngeal transit time by electrical impedance tomography, Clin. Phys. Physiol. Meas., 1993, vol. 13, Suppl. A, pp. 197-200.

Rols, et al, Highly efficient transfection of mammalian cells by electric field pulses application to large volumes of cell culture by using a flow system, Eur. J. Biochem, 1992, 205, pp. 115-121.

Brown, et al, Blood flow imaging using electrical impedance tomography, Clin. Phys. Physiol. Meas., 1992, vol. 13, Suppl. A, pp. 175-179.

Foster, et al, Production of prostatic lesions in canines usign transrectally administered high-intensity focused ultrasound, Eur Urol, 1993, pp. 330-336.

Shiina, et al, Percutaneous ethanol injection therapy for hepatocellular carcinoma: Results in 146 patients, AJR, May 1993, 160, pp. 1023-1028.

Salford, et al, A new brain tumour therapy combining bleomycin with in vivo electropermeabilization, Biochemical and Biohysical Research Communications, Jul. 30, 1993, vol. 194, No. pp. 938-943.

Glidewell, Ng, The use of magnetic resonance imaging data and the inclusion of anisotropic regions in electrical impedance tomography, ISA, 1993, pp. 251-257.

Gascoyne, et al, Membrane changes accompanying the induced differentiation of Friend murine erythroleukemia cells studied by dielectrophoresis, Biochimca et Biophysica Acta, 1993, 1149, pp. 119-126.

Foster, et al, High-intensity focused ultrsound in the treatment of prostatic disease, Eur Urol, 1993, 23(suppl1), pp. 29-33.

Andreason, Electroporation as a technique for the ransfer of macromolecules into mamalian cell lines, J. Tiss. Cult. Meth., 1993, 15, pp. 56-62.

Weaver, Electroporation: A general phenomenon for manipulating cells and tissues, Journal of Cellular Biochemistry, 1993, 51, pp. 426-435.

Barber, Electrical impedance tomography applied potential tomography, Advances in Biomedical Engineering, 1993, IOS Press, pp. 165-173.

Cook, et al, ACT3: a high-speed, high-precision electrical impedance tomograph, IEEE Transactions on Biomedical Engineering, 1994, vol. 41, No. 8, pp. 713-722.

Alberts, et al, Molecular biology of the Cell, Biocchemical education, 1994, 22(3), pp. 164.

Hughes, et al, An analysis of studies comparing electrical impedance tomography with x-ray videofluoroscopy in the assessment of swallowing, Physiol. Meas. 1994, 15, pp. A199-A209.

Mazurek, et al, Effect of Short HV Pulses in Bacteria and Fungi, 1995, vol. 2, No. 3, pp. 418-425.

Griffiths, Tissue spectroscopy with electrical impedance tomography: Computer simulations, IEEE Transactions on Biomedical Engineering, Sep. 1995, vol. 42, No. 9, pp. 948-954.

Gencer, et al, Electrical impedance tomography: Induced-currentimaging achieved with a multiple coil system, IEEE Transactions on Biomedical Engineering, Feb. 1996, vol. 43, No. 2, pp. 139-149.

Weaver, Chizmadzhev, Theory of electroporation: a review, Biolectrochemistry and Bioenergetics, 1996, vol. 41, pp. 135-160.

Gimsa, et al, Dielectric spectroscopy of single human erythrocytes at physiological ionic strength: Dispersion of the cytoplasm, Biophysical Journal, Jul. 1996, vol. 71, pp. 495-506.

Choi, et al, Preclinical analysis of irreversible electroporation on rat liver tissues using a microfabricated electroporator, Tissue Engineering Part C, 2010, vol. 16, No. 6, pp. 1245-1253.

Neal, et al, Treatment of breast cancer through the application of irreversible electroporation using a novel minimally invasive single needle electrode, Breat Cancer Res Treat, Aug. 27, 2010, 123, 1, pp. 295-301.

Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-432.

Lee, et al, Irreversible electroporation: A novel image-guided cancer therapy, Gut and Liver, Sep. 2010, vol. 4, Supp. 1, pp. S99-S104.

Carmi, Georgiades, Combination percutaneous and intraarterial therapy for the treatment of hepatocellular carcinoma: A review, Seminars in Interventional Radiology, 2010, vol. 27, No. 3, pp. 296-301.

Mahmood, Gehl, Optimizing clinical performance and geometrical robustness of a new electrode device for intracranial tumor electroporation, Bioelectrochemistry, Jan. 6, 2011, 81, pp. 10-16.

Guo, et al, Irreversible electroporation in the liver: Contrast-enhanced inversion-recovery MR imaging approaches to differentiate reversibly electroporated penumbra from irreversibly electroporated ablation zones, Radiology, Feb. 2011, vol. 258, No. 2, pp. 461-468.

Nesin, et al, Manipulation of cell volume and membrane pore comparision following single cell permeabilization with 60- and 600-ns electric pulses, Biochim Biophys Acta, Mar. 2011, 1808(3), pp. 792-801.

Mahmood, et al, Diffusion-weighted MRI for verification of electroporation-based treatments, J Membrane Biol, Mar. 3, 2011, 240, pp. 131-138.

Thomson, et al, Investigation of the safety of irreversible electroporation in humans, J Vasc Interv Radiol, May 2011, 22, pp. 611-621.

Rossmeisl, Jr., et al, Successful treatment of a large soft tissue sarcoma with irreversible electroporation, Journal of Clinical Oncology, May 1, 2011, vol. 29, No. 13, pp. e372-e377.

Arena, et al, High-frequency irreversible electroporation (H-FIRE) for non-thermal ablation without muscle contraction, BioMedical Engineering Online, Nov. 21, 2011, 10: 102, pp. 1-20.

Szot, et al, 3D in vitro bioengineered tumors based on collagen I hydrogels, Biomaterials, Nov. 2011, 32(31), pp. 7905-7912.

Sano, et al, Modeling and development fo a low frequency contactless dielectrophoresis (cDEP) platform to sort cancer cells from dilute whole blood samples, Biosensors and Bioelectronics, 2011, pp. 1-8.

Salmanzadeh, et al, Dielectrophoretic differentiation of mouse ovarian surface epithelial cells, macrophages, and fibroblasts using contactless dielectrophoresis, Biomicrofluidics, Apr. 3, 2012, 6, 024104, pp. 1-13.

Arena, et al, Phase change electrodes for reducing joule heating during irreversible electroporation, Proceedings of the ASME 2012 Summer Bioengineering Conference, Jun. 20, 2012, pp. 1-2.

Weaver, et al, A brief overview of electroporation pulse strength-duration space: A region where additional intracellular effects are expected, Bioelectrochemistry, Oct. 2012, 87, pp. 236-243.

(56) References Cited

OTHER PUBLICATIONS

Bagla, Papadouris, Percutaneous irreversible electroporation of surgically unresectable pancreatic cancer: A case report, J Vasc Interv Radiol, 2012, 23, pp. 142-145.
Phillips, et al, Irreversible electroporation on the small intestine, British Journal of Cancer, 2012, pp. 1-6.
Mahnic-Kalamiza, et al, Educational application for visualization and analysis of electric field strength in multiple electrode electroporation, BMC Medical Education, 2012, 12, 102, pp. 1-13.
Lebar, Miklavcic, Cell electropermeabilization to small molecules in vitro: control by pulse parameters, Radiol ONCOL, 2001, 35, 3, pp. 193-202.
Naslund, Cost-effectiveness of minimally invasive treatments and transurethral resection (TURP) in benign prostatic hyperplasia (BPH), Unveristy of Maryland School of Medicine, 2001, pp. 1213.
Davalos, et al, A feasibility study for electrical impedance tomography as a means to montior tissue electroporatioin or molecular medicien, IEEE Transactions on Biomedical Engineering, Apr. 2002, vol. 49, No. 4, pp. 400-403.
Jossinet, et al, Electrical impedance end-tomography: Imaging tissue from inside, IEEE Transactions on Medical Imaging, Jun. 2002, vol. 21, No. 6, pp. 560-565.
Lebar, et al, Inter-pulse interval between rectangular voltage pulses affects electroporation threshold of artifical lipid bilayers, IEEE Transactions on Nanobioscience, Sep. 2002, vol. 1, No. 3, pp. 116-120.
Sersa, et al, Reduced blood flow and oxygenation in SA-I tumors after electrochemotherapy with cisplatin, 2003, 87, pp. 1047-1054.
Davalos, Real-time imaging for molecular medicine through electrical impedance tomography of electroporation, Dissertation, Univeristy of California, Berkeley (2002).
Wright, On a relationship betweene the arrhenius parameters from thermal damage studies, Technical Brief, Journal of Biomechanical Engineering, Transactions of the ASME, Apr. 2003, vol. 125, pp. 300-304.
Heczynska, et al, Hypoxia promotes a dedifferentiated phenotype in ductal breast carcinoma in situ, Cancer Research, Apr. 1, 2003, 63, pp. 1441-1444.
Ivorra, Bioimpedance monitoring for physicians: an overview, Biomedical Applications Group, Centre Nacional de Microelectronica, Jul. 2003, pp. 1-35.
Weaver, Electroporation of biological membranes from multicellular to nano scales, IEEE Transactions on Dielectrics and Electrical Insulation, Oct. 2003, vol. 10, No. 5, pp. 754-768.
Dev, et al, Electric field of a six-needle array electrode used in drug and DNA delivery in vivo: Analytical versus numerical solution, IEEE Transactions on Biomedical Engineering, Nov. 2003, vol. 50, No. 11, pp. 1296-1300.
Rajagopal, Rockson, Coronary restenosis: A review of mechanisms and management, The American Journal of Medicine, Nov 2003, vol. 115, pp. 547-553.
Bersa, et al, Tumor blood flow modifying effects of electrochemotherapy: a potential vascular targeted mechanism, Radiol Oncol, 2003, 37, 1, pp. 43-48.
Davalos, et al, Theoretical analysis of the thermal effects during in vivo tissue electroporation, Bioelectrochemistry, 2003, 61, pp. 99-107.
Gothelf, et al, Electrochemotherapy: results of cancer treatment using enhanced delivery of bleomycin by electroporation, Cancer Treatment Reviews, 2003, 39, pp. 371-387.
Bancroft, et al, Design of a flow perfusion bioreactor system for bone tissue-engineering applications, Tissue Engineering, 2003, vol. 9, No. 3, pp. 549-554.
Malpica, et al, Grading ovarian serous carcinoma using a two-tier system, Am J Surg Pathol, Apr. 2004, vol. 28, No. 4, pp. 496-504.
Davalos, et al, Electrical impedance tomography for imaging tissue electroporation, IEEE Transactions on Biomedical Engineering, May 2004, vol. 51, No. 5, pp. 761-767.
Albright, et al, Performance and complicatioins associated with the Synchromed 10-ml infusion pump for intrathecal baclofen administration in children, J Neurosurg (Pediatrics 2), Aug. 2004, vol. 101, pp. 64-68.
Diederich, et al, Catheter-based ultrasound applicators for selective thermal ablation: progress towards MRI-guided applications in prostate, Int. J. Hyperthermia, Nov. 2004, vol. 20, No. 7, pp. 739-756.
Radeva, et al, Induction of apoptosis and necrosis in cancer cells by electric fields, electromagnetic fields, and photodynamically active quinoids, Electromagnetic Biology and Medicine, 2003, 23, pp. 185-200.
Davalos, et al, Tissue ablation with irreversible electroporation, Annals of Biomedical Engineering, Feb. 2005, vol. 33, No. 2, pp. 223-231.
Sel, et al, Sequential finite element model of tissue electropermeabilization, IEEE Transactions on Biomedical Engineering, May 2005, vol. 52, No. 5, pp. 816-827.
Dean, Nonviral gene transfer to skeletal, smooth, and cardiac muscle in living animals, Am J Physiol cell Physiol, Aug. 2005, 289, pp. C233-C245.
Pavselj, et al, the course of tissue permeabilization studied on a mathematical model of a subcutaenous tumor in small animals, IEEE Transactions on Biomedical Engineering, Aug. 2005, vol. 52, No. 8, pp. 1373-1381.
Paszek, et al, Tensional homeostasis and the malignant phenotype, Cancer Cell, Sep. 2005, vol. 8, pp. 241-254.
Saur, et al, CXCR4 expression increases liver and lung metastasis in a mouse model of pancreatic cancer, Basic-Liver, pancreas, and biliary tract, Gastroenterology, Oct. 2004, 129, pp. 1237-1250.
Knight, et al, Direct imaging of transvenous radiofrequency cardiac ablation using a steerable fiberoptic infrared endoscope, Heart Rhythm Society, Oct. 2005, vol. 2, No. 10, pp. 1116-1121.
Miller, et al, Cancer cells ablation with irreversible electroporation, Technology in Cancer Research and Treatment, Dec. 2005, vol. 4, No. 6, pp. 699-705.
Mir, et al, Electric pulse-mediated gene delviery to various animal tissues, Advances in Genetics, 2005, vol. 54, pp. 84-114.
Nikolski, Efimov, Electroporation of the heart, Europace, 2005, 7, pp. S146-S154.
Machado-Aranda, et al, Gene transfer of the Na+, K+K-ATPase B1 subunit using electroporation increases lung iquid clearance, American Journal of Respiratory and Critical Care Medicine, 2004, vol. 171, pp. 204-211.
Kotnik, Miklavcic, Theoretical evaluation of voltage inducement on internal membranes of biological cells exposed to electric fields, Biophysical Journal, Jan. 2006, vol. 90, pp. 480-491.
Labeed, et al, Differences in the biophysical properties of membrane and cytoplasm of apoptotic cells revealed using dielectrophoresis, Biochimica et Biophysica Acta, Feb. 23, 2006, 1760, pp. 922-929.
Pucihar, et al, Numerical determination of transmembrane voltage indcued on irregularly shaped cells, Annals of Biomedical Engineering, Mar. 18, 2006, vol. 34, No. 4, pp. 642-652.
Gilbert, et al, Decellularization of tissues and organs, Biomaterials, Mar. 7, 2006, 27, pp. 3675-3683.
Edd, et al, In vivo results of a new focal tissue ablation technique: Irreversible electroporation, IEEE Transactions on Biomedical Engineering, Jun. 2006, vol. 53, No. 5, pp. 1409-1415.
Ivorra, Rubinsky, Impedance analyzer for in vivo electroporation studies, Proceedings of the 28th IEEE EMBS Annual International Conference, IEEE, Aug. 30, 2006, pp. 5056-5059.
Carpenter, et al, CellProfiler: image analysis software for identifying and quantifying cell phenotypes, Genome Biology, Oct. 31, 2006, vol. 7, Iss. 10, R100, pp. 1-11.
Kanduser, et al, Cell membrane fluidity related to electroporation and resealing, Eur Biophys J, Oct. 8, 2006, 35, pp. 196-204.
Bolland, et al, Development and characterisation of a full-thickness acellular porcine bladder matrix for tissue engineering, Biomaterials, Nov. 7, 2006, 28, pp. 1061-1070.
Cukjati, et al, Real time electroporation control for accurate and safe in vivo non-viral gene therapy, Bioelectrochemistry, Nov. 10, 2006, 70, pp. 501-507.

(56) References Cited

OTHER PUBLICATIONS

Tijink, et al, How we do it: Chemo-electroporation in the head and neck for otherwise untreatable patients, Correspondence, Clinical Otolaryngology, 2006, 31, pp. 447-451.

Viarty, et al, Electrochemotherapy—An easy, highly effective and safe treatment of cutaneous and subcutaneous metastases: Results of ESOPE (European Standard Operating Procedures of Electrochemotherapy) study, EJC Supplements, 2006, 4, pp. 3-13.

Soden, et al, Successful application of targeted electrochemotherapy using novel flexible electrodes and low dose bleomycin to solid tumors, Cancer Letters, 2006, 232 pp. 300-310.

Demirbas, Thermal energy storage and phase change materials: An overview, Energy Sources, Part B, 2006, 1, pp. 35-95.

Rubinsky, et al, Irreversible electroporation: A new ablation modality—Clinical implications, Technology in Cancer Research and Treatment, Feb. 2007, vol. 6, No. 1, pp. 1-12.

Zhou, et al, Electroporation-mediated transfer of plasmids to the lung results in reduced TLR9 signaling and inflammation, Gene Therapy, Mar. 8, 2007, 14, pp. 775-780.

Lavee, et al, A novel nonthermal energy source for surgical epicardial atrial ablation: Irreversible electroporation, The Heart Forum, Mar. 2007, 10, 2, pp. 96-101.

adEYANJU, et al, The improvement of irreversible electroporation therapy using saline-irrigated electrodes: A theoretical study, Technology in Cancer Research and Treatment, Aug. 2011, vol. 10, No. 4, pp. 347-360.

Maor, Rubinsky, Endovascular nonthermal irreversible electroporation: A finite element analysis, Journal of Biomedical Engineering, Feb. 7, 2010, vol. 132, 031008, pp. 1-7.

Choi, et al, Preclinical analysis of irreversible electroporation on rat liver tissues using a microfabricated alectroporator, Tissue Engineering Part C, 2010, vol. 16, No. 6, pp. 1245-1253.

Verbridge, et al, Oxygen-controlled three-dimensional cultures to analyze tumor angiogenesis, Tissue Engineering, Part A, Apr. 9, 2010, vol. 16, No. 7, pp. 2133-2141.

Lee, et al, Advanced hepatic ablation technique for creating complete cell death: Irreversible electroporation, 2010, Radiology, vol. 255, No. 2, pp. 426-433.

Ball, et al, Irreversible electroporation: A new challenge in "out of the operating theater" anesthesia, Anesth Analg, May 2010, 110, pp. 1305-1309.

Laufer, et al, Electrical impedance characterization of normal and cancerous human hepatic tissue, Physiol Meas, 2010, 31, pp. 995-1009.

Sabuncu, et al, Dielectrophoretic separation of mouse melanoma clones, Biomicrofluidics, Jun. 16, 2010, 4, 021101, pp. 1-7.

Garcia, et al, Intracranial nonthermal irreversible electroporation: In vivo analysis, J Membrane Biol, Jul. 29, 2010, 236, pp. 127-136.

Nieal, et al, Treatment of breast cancer through the application of irreversible electroporation using a novel minimally Invasive single needle electrode, Breat Cancer Res Treat, Aug. 27, 2010, 123, 1, pp. 295-301.

Zhang, et al, MR imaging to assess immediate response to irreversible electroporation for targeted ablation of liver tissues: Preclinical feasibility studies in a rodent model, Radiology, Aug. 2010, vol. 256, No. 2, pp. 424-32.

Neal, et al, A study using irreversible electroporation to treat large, irregular tumors in a canine patient, 32nd Annual International Conference of the IEEE EMBS, IEEE, Aug. 2010, pp. 2747-2750.

Garcia, et al, Non-thermal irreversible electroporation for deep intracranial disorders, 32nd Annual International Conferenece of the IEEE EMBS, IEEE, Aug. 2010, pp. 2747463-.

Phillips, et al, Nonthermal irreversible electroporation for tissue decellularization, Journal of Biomedical Engineering, Aug. 16, 2010, vol. 132, 091003, pp. 1-8.

Pech, et al, Irreversible electroporation of renal cell carcinoma: A first-in-man phase I clinical study, Cardiovasc Intervent Radiol, Aug. 15, 2010.

Lee, et al, Irreversible electroporation: A novel image-guided cancer therapy, Gut and Liver, Sep. 2010, vol. 4, Supp. 1, pp. S99-104.

Hong, et al, Cardiac ablation via electroporation, 31st Annual International Conference of the IEEE EMBS, IEEE, Sep. 2, 2010, pp. 3381-3384.

Dupuy, et al, Irreversible electroporation in a swine lung model, Cardiovasc Intervent Radiol, Dec. 30, 2010, 34, pp. 391-395.

Arena, et al, Theoretical considerations of tissue electropration with high frequency biopolar pulses, IEEEE, pp. 1-7, (2010).

Deodhar, et al, Renal tissue ablation with irreversible electroporation: Preliminary results in a porcine model, Technology and Engineering, Urology, 2010, 1-7.

McCarley, Soulen, Percutaneous ablation of hepatic tumors, Seminars in Interventional Radiology, 2010, vol. 27, No. 3, pp. 255-260.

Neu, Neu, Mechanism of irreversible electroporation in cells: Insight from the models, Irreversible Electroporation: Biomed, pp. 85-122, (2010).

Charpentier, et al, Irreversible electroporation of the pancreas in swine: A pilot study, HPB, 2010, 12, pp. 348-351.

Tracy, et al, Irreversible electroporation (IRE): A novel method for renal tissue ablation, BJU International, 107, pp. 1982-1987.

Onik, Rubinsky, Irreversible electroporation: First patient experience focal therapy of prostate cancer, Irreversible Electroporation, Biomed, pp. 235-247, (2010).

McWilliams, et al, Image-guided tumor ablation: Emerging technologies and future directions, Seminars in Interventional Radiology, 2010, vol. 27, No. 3, pp. 302-313.

Kurup, Callstrom, Image-guided percutaneous ablation of bone and soft tissue tumors, Seminars in Interventional Radiology, 2010, vol. 27, No. 3, pp. 276-284.

Thomson, Human experience with irreversible electroporation, Irreversible Electroporation, BIOMED, 2010, pp. 249-354.

Saldanha, et al, Current tumor ablation technologies: Basic science and device review, Seminars in Interventional Radiology, 2010, vol. 27, No. 3, pp. 247-254.

Dupuy, Shulman, Current status of thermal ablation treatments for lung malignancies, Seminars in Interventional Radiology, 2010, vol. 27, No. 3, pp. 268-275.

Carmi, Georgiades, Combination percutaneous and intraarterial therapy for the treatment of hepatocellular aarcinoma: A review, Seminars in Interventional Radiology, 2010, vol. 27, No. 3, pp. 296-301.

Jarm, et al, Antivascular effects of electrochemotherapy: implicatoins in treatment of bleeding metastases, Expert Rev. Anticancer Ther., 2010, 10, 5, pp. 729-746.

Maybody, An overview of image-guided percutaneous ablation of renal tumors, Seminars in Interventional Radiology, 2010, vol. 27, No. 3, pp. 261-267.

Goldberg, Rubinsky, A statistical model for multidimensional irreversible electroporation cell death in tissue, Biomedical Engineering Online, 2010, 9;13, pp. 1-13.

Sano, et al, Towards the creation of decellularized organ constructs using irreversible electroporation and active mechanical perfusion, Biomedical Engineering Online, 2010, 9, 83, pp. 1-16.

Mahmood, Gehl, Optimizing clinical performance and geometrical robustness of a new electrode device for ntracranial tumor electroporation, Bioelectrochemistry, Jan. 6, 2011, 81, pp. 10-16.

Garcia, et al, Non-thermal irreversible electroporation (N-TIRE) and adjuvant fractionated radiotherapeutic multimodal therapy for intracranial malignant glioma in a canine patient, Feb. 2011, vol. 10, No. 1, pp. 73-83.

Guo, et al, Irreversible electroporation in the liver: Contrast-enhanced inversion-recovery MR imaging approaches to lifferentiate reversibly electroporated penumbra from irreversibly electroporated ablation zones, Radiology, Feb. 2011, vol. 258, No. 2, pp. 461-468.

Bower, et al, Irreversible electroporation of the pancreas: Definitive local therapy without systemic effects, Journal of Surgical Oncology, Feb. 28, 2011, 104, pp. 22-28.

Ellis, et al, Nonthermal irreversible electroporation for intracranial surgical applications, J Neurosurg, Mar. 2011, 114, pp. 681-688.

Nesin, et al, Manipulation of cell volume and membrane pore comparision following single cell permeabilization with 60- and 600-ns. electric pulses, Biochim Biophys Acta, Mar. 2011, 1808(3), pp. 792-801.

(56) References Cited

OTHER PUBLICATIONS

McCall, Nanoknife, liposomal doxorubicin show efficacy against liver cancer, European Congress of Radiology, Mar. 1, 2011, pp. 1-2.

Viahmood, et al, Diffusion-weighted MRI for verification of electroporation-based treatments, J Membrane Biol, Mar. 6, 2011, 240, pp. 131-138.

Deodhar, et al, Irreversible electroporation near the heart: Ventricular arrhythmias can be prevented with ECG synchronization, AJR, Mar. 2011, 196, pp. W330-W335.

Garcia, et al, A parametric study delineating irreversible electroporation from thermal damage based on a minimally invasive intracranial procedure, Biomedical Engineering Online, 2011, 10: 34, pp. 1-21.

Li, et al, The effects of irreversible electroporation (IRE) on nerves, PLOS One, Apr. 14, 2011, vol. 6, Iss. 4, e18831, pp. 1-7.

Neal, et al, Successful treatment of a large soft tissue sarcoma with irreversible electroporaiton, Journal of Clinical Oncology, May 1, 2011, vol. 29, No. 13, pp. e372-e377.

Thomson, et al, Investigation of the safety of irreversible electroporation in humans, J Vasc Intern Radio!, May 2011, 22, pp. 611-621.

Rossmeisl, Jr., et al, Successful treatment of a large soft tissue sarcoma with irreversible electroporation, Journal pf Clinical Oncology, May 1, 2011, vol. 29, No. 13, pp. e372-e377.

Daniels, Rubinsky, Temperature modulation of electric fields in biological matter, PLOS One, vol. 6, Iss. 6, a20877, pp. 1-9, Jun. 2011.

Lion, et al, Poly(I:C) enhances the susceptibility of leukemic cells to NK cell cytotoxicity and phagocytosis by DC, PLOS One, vol. 6, Iss. 6, e20952, pp. 1-10, Jun. 17, 2011.

Agerholm-Larsen, et al, Preclinical validation of electrochemotherapy as an effective treatment for brain tumors, Cancer Res, Jun. 1, 2011, 71, 11, pp. 3753-3762.

Mulhall, et al, Cancer, pre-cancer and normal oral cells distinguished by dielectrophoresis, Anal Bioanal chem, Aug. 30, 2011, 401, pp. 2455-2463.

Troszak, Rubinsky, Self-powered electroporation using a singularity-induced nano-electroporation configuration, Biochemical and Biophysical Research Communications, Sep. 28, 2011, 414, pp. 419-424.

Arena, et al, High-frequency irreversible electroporation (H-FIRE) for non-thermal ablation without muscle aontraction, BioMedical Engineering Online, Nov. 21, 2011, 10: 102, pp. 1-20.

Hjouj, et al, Electroporationo-induced BBB disruption and tissue damage depicted by MRI, Neuro-Oncology, Abstracts from the 16th Annual Scientific Meeting, Nov. 17, 2011, vol. 13, Supp 3, ET-32, p. iii114.

Szot, et al, 3D in vitro bioengineered tumors based on collagen I hydrogels, Biomaterials, Nov. 2011, 32(31), pp. 1905-7912.

Bastista, et al, The use of whole organ decellularization for the generation of a vascularized liver organoid, Hepatology, 2011, vol. 53, No. 2, pp. 604-617.

Sano, et al, Modeling and development fo a low frequency contactless dielectrophoresis (cDEP) platform to sort aancer cells from dilute whole blood samples, Biosensors and Bioelectronics, 2011, pp. 1-8.

Charpentier, et al, Irreversible electroporation of the liver an dliver hilum in swine, HBP, 2011, 13, pp. 168-173.

Sankaranarayanan, et al, Effect of irreversible electroporation on cell proliferation in fibroblasts, Proc. ESA Annual Meeting on Electrostatics, 2011, pp. 1-8.

Sano, et al, Contactless dielectrophoretic spectroscopy: Examination of the dielectric properties of cells found in blood, Electrophoresis, 2011, 32, pp. 3164-3171.

Chen, et al, Classification of cell types using a microfluidic device for mechanical and electrical measurements on single cells, Lab Chip, 2011, 11 , pp. 3174-3181.

Rebersek, Miklavcic, Advantages and disadvantages of different concepts of electroporation pulse generation, Automatika, 2011, 52, 1, pp. 12-19.

Ben-David, et al, Characterization of irreversible electroporaiton ablation in in vivo porcine liver, AJR, Jan. 2012, 198, pp. W62-W68.

Appelbaum, et al, US findings after irreversible electroporation ablation: Radiologic-pathologic correlation, Radiology, Jan. 2012, vol. 262, No. 1, pp. 117-125.

Salmanzadeh, et al, Dielectrophoretic differentiation of mouse ovarian surface epithelial cells, macrophages, and ibroblasts using contactless dielectrophoresis, Biomicrofluidics, Apr. 3, 2012, 6, 024104, pp. 1-13.

Neal, et al, Experimental characterization and numerical modeling of tissue electrical conductivity during pulsed electric fields for irreversible electroporation treatment planning, IEEE Transactions on Biomedical Engineering, Apr. 2012, vol. 59, No. 4, pp. 1076-1085.

Du Pre, et al, Minimal coronary artery damage by myocardial electroporation ablation, European Society of cardiology, Europace, May 31, 2012, pp. 1-6.

Wittkampf, et al, Myocradial lesion depth with circular electroporation ablation, Circ Arrhythm Electrophysiol, 2012, 5, pp. 581-586.

Arena, et al, Phase change electrodes for reducing joule heating during irreversible electroporation, Proceedings of be ASME 2012 Summer Bioengineering Conference, Jun. 20, 2012, pp. 1-2.

Garcia, et al, Towards a predictive model of electroporation-based therapies using pre-pulse electrical measurements, 34th Annual International Conference of the IEEE EMBS, Aug. 28, 2012, pp. 2575-2578.

Hjouj, et al, MRI study on reversible and irreversible electroporation induced blood brain barrier disruption, Aug. 10, 2012, PLOS One, vol. 7, 8, e42817, pp. 1-9.

Martin, et al, Irreversible electroporation therapy in the management of locally advanced pancreatic adenocarcinoma, American College of Surgeons, Sep. 2012, vol. 215, No. 3, pp. 361-369.

Weaver, et al, A brief overview of electroporation pulse strength-duration space: A region where additional ntracellular effects are expected, Bioelectrochemistry, Oct. 2012, 87, pp. 236-243.

Arena, et al, A three-dimensional in vitro tumor platform for modeling therapeutic irreversible electroporation, Biophysical Journal, Nov. 2012, vol. 103, pp. 2033-2042.

Garcia, et al, 7.0-T magnetic resonance imaging characterization of acute blood-brain-barrier disruption achieved with intracranial irreversible electroporation, PLOS One, vol. 7, 11, pp. 1- 8, Nov. 30, 2012.

Arena, et al, Towards the development of latent heat storage electrodes for electroporation-based therapies, Applied Physics Letters, 2012, 101, 083902, pp. 1-4.

Cannon, et al, Safety and early efficacy of irreversible electroporation for hepatic tumors in proximity to vital structures, Journal of Surgical Oncology, 2012, pp. 1-6.

Bagla, Papadouris, Percutaneous irreversible electroporation of surgically unresectable pancreatic cancer: A case report, J Vasc Intery Radiol, 2012, 23, pp. 142-145.

Phillips, et al, Irreversible electroporation on the small intestine, British Journal of Cancer, 2012, ppp. 1-6.

Viahnic-Kalamiza, et al, Educational application for visualization and analysis of electric field strength in multiple electrode electroporation, BMC Medical Education, 2012, 12, 102, pp. 1-13.

Kingham, et al, Ablation of perivascular hepatic malignant tumors with irreversible electroporation, J Am Coll Surg, 2012, 215, pp. 379-387.

Salmanzadeh, et al, Investigating dielectric properties of different stages of syngeneic murine ovarian cancer cells, Biomicrofluidics, Jan. 23, 2013, 7, 011809, pp. 1-12.

Maybody, An Overview of Image-Guided Percutaneous Ablation of Renal Tumors, Seminars in Interventional Radiology/vol. 27, No. 3, 2010, pp. 261-267.

Carmi, et al, Combination Percutaneous and Intraarterial Therapy for the Treatment of Hepatocellular Carcinoma: A Review, Semin Intervent Radiol 2010, 27:296-301.

(56) References Cited

OTHER PUBLICATIONS

Saldanha, et al, Current Tumor Ablation Technologies: Basic Science and Device Review, Semin Intervent Radiol 2010, 27:247-254.
Kurup, et al, Image-Guided Percutaneous Ablation of Bone and soft Tissue Tumors, Semin Intervent Radiol 2010, 27:276-284.
McCarley, et al, Percutaneous Ablation of Hepatic Tumors, Semin Intervent Radiol 2010, 27: 255-260.
Organ, Electrophysiologic Principles of RF Lesion Making, Int. Symp. Radiofrequency Lesion Making Procedures, 1976, pp. 69-76.
Onik, et al, Sonographic Monitoring of Hepatic Cryosurgery in an Experimental Animal Model, American Roentgen Ray Society, 1985, pp. 1043-1047.
Foster, et al, Production of Prostatic Lesions in Canines Using Transrectally Administered High-Intensity Focused Ultrasound, Eur Urol 1993, pp. 330-336.
Foster, et al, High-Intensity Focused Ultrasound in the Treatment of Prostatic Disease, Eur Urol 1993, pp. 29-33.
Lorentze, The Loop Electrode: In Vivo Evaluation of a Device for Ultrasound-Guided Interstitial Tissue Ablation Using RF Electrosurgery, Acad Radiol, pp. 219-224, Mar. 1996.
Lorentze, A Cooled Needle Electrode for Rf Tissue Ablation: Thermodynamic Aspects of Improved Performance Compared with Conventional Needle Design, Acad Radiol, pp. 556-563, Jul. 1996.
Zlotta, et al, Possible Mechanisms of Action of Transurethral Needle Ablation of the Prostate on Benign Prostatic Hyperplasia Symptoms: A Neurohistochemical Study, Journal of Urology, Mar. 1997.
Lorentze, et al, RF Tissue Ablation with a Cooled Needle in Vitro: Ultrasonography, Dose Response and Lesion Temperature, Acad Radiol, pp. 292-297, Apr. 1997.
Naslund, Transurethral Needle Ablation of the Prostate, Urology 1997, pp. 167-172, Aug. 1997.
Rubinskey, Cryosurgery, Annu. Rev. Biomed. Eng. 2000, 02: pp. 157-187, Jul. 1998.
Carson, et al, BPH Management Strategies, Urology Times, vol. 29, Supplemental 1, May 2001.
Niaslund, et al, Cost-effectiveness of Minimally Invasive Treatments and Transurethral Resection in Benign Prostatic Hyperplasia, AUA National Meeting, 2001, pp. 1213.
Zlotta, et al, Long-term Evaluation of Transurethral NEedle Ablation of the Prostate for Treatment of Benign Prostatic Hyperplasia: Clinial Outcomes After 5 Years, AUA National Meeting, 2001, pp. 1024.
ViaMed, Inc. Office TUNA System clinical trail summary, 2001.
Chandrasekar, et al, Transurethral Needle Ablation of the Prostate—A Prospective Study, Six Year Follow Up, AUA National Meeting, 2001, pp. 1210.
ViaMed, Inc. Office TUNA System Patient Brochure, 2001.
Lee, RadioFrequency Ablation of Uterine Leiomyomata: A New Minimally Invasive Hysterectomy Alernative, Tuesday Papers, vol. 99, No. 4 (Supplement), 2002, pp. 9S.
Chang, Finite Elemenet Analysis of Hepatic RF Ablation Probes using Temperature-Dependent Electical Conductivity, BioMedical Engineering OnLine 2003, 2:12.
Schmedt, et al, Evaluation of Endovenous RF Ablation and Laser Therapy with Endoluminal Optical Coherence Tomography in an Ex Vivo Model, The Society for Vascular Surgery 2007, pp. 1047-1058.
Knight, et al, Direct Imaging of Transvenous RF Cardiac Ablation Using a Streerable Fiberoptic Infrared Endoscope, Heart Shythm Society, 2005, pp. 1116-1121.
Bruners, et al, A Newly Developed Perfused Umbrella Electrode for RF Ablation: An Ex Vivo Evaluation Study in Bovine Liver, Cardiovasc Intervent Radiol, 2007, pp. 992-998.
Dulucq, et al, Virtually Bloodless Laparoscopic Liver Resection of Recurrent Hepatoma With a New Laparoscopic Sealer Device, Surg Laparosc Endoc Percutan Tech, 2007, pp. 413-415.
Recaldini, Percutaneous Sonographically Guided RF Ablation of Medium-Sized Fibroids: Feasibility Study, AJR:189, 2007, pp. 1303-1306.
Lee, et al, Multiple-Electrode RF Ablation of in Vivo Porcine Liver, Investigative Radiology, pp. 676-683, Oct. 2007.
Park, et al, Prognostic Factors Influencing the Development of an Iatrogenic Pneumothorax for CT-Guided RF Ablation of Upper Renal Tumor, Acta Radiologica, 2008, pp. 1200-1206.
Gervais, et al, Society of Interventional Radiology Position Statement on Percutaneous RF Ablation for the Treatment of Liver Tumors, 2009, J Vasc Intery Radiol, pp. 3- 8.
Thanos, Image-Guided RF Ablation of a Pancreatic Tumor with a New Triple Spiral-Shaped Electrode, Cardiovasc Intervent Radiol, 2010, pp. 215-218.
Carrafiello, et al, Ultrasound-Guided RF Thermal Ablation of Uterine Fibroids: Medium-Term Follow-Up, Cardiovasc Intervent Radiol, 2010, pp. 113-119.
Majid, An Overview of Image-Guided Percutaneous Ablation of Renal Tumors, Semin Intervent Radiol 2010, pp. 261-267.
Carmi, et al, Combination Percutaneous and Intraarterial Therapy for the Treatment of Hepatocullular Carcinoma: A Review, Semin Intervent Radiol 2010, pp. 296-301.
Howenstein, et al, Complications of RF Ablation of Hepatic, Pulmonary, and Renal Neoplasms, Semin Intervent Radiol 2010, pp. 285-295.
Dupuy, et al, Current Status of Thermal Ablation Treatments for Lung Malignancies, Semin Intervent Radiol 2010, pp. 268-275.
Saldanha, et al, Current Tumor Ablation Technologies: Basic Science and Device Review, Semin Intervent Radiol 2010, pp. 247-254.
Kurup, et al, Image-Guided Percutaneous Ablation of Bone and Soft Tissue Tumors, Semin Intervent Radiol 2010, pp. 276-284.
McWilliams, et al, Image-Guided tumor Ablation: Emerging Technologies and Future Directions, Semin Intervent Radiol 2010, pp. 302-313.
McCarley, Percutaneous Ablation of Hepatic Tumors, Semin Intervent Radiol 2010, pp. 255-260.
DeBenedectis, et al, Utility of Iodinated Contrast Medium in Hydrodissection Fluid when Performing Renal Tumor Ablation, J Vasc Intery Radiol 2010, pp. 745-747.
Cha et al, RF Ablation Using a New Type of Interally Cooled Electrode With an Adjustable Active Tip: An Experimental Study in Ex Vivo Bovine and in Vivo Porcine Livers, European Journal of Radiology, 2011, pp. 516-521.
McCall, NanoKnife, Liposomal Doxorubicin Show Efficacy Against Liver Cancer, European Congress of Radiology 2011.
Cowley, Lifestyle Good news for boomers, Newsweek, Dec. 30, 1996.
Sharma, et al, Poloxamer 188 decrease susceptibility of artificial lipid membranes to electroporation, Biophysical Journal, 1996, vol. 71, pp. 3229-3241.
Blad, Baldetorp, Impedance spectra of tumour tissue in comparison with normal tissue; a possible clinical application for electrical impedance tomography, Physiol. Meas., 1996, 17, pp. A105-A115.
Ho, Mittal, Electroporation of cell membranes: a review, Critical Reviews in Biotechnology, 1996, 16(4), pp. 349-362.
Gilbert, et al, Rapid report novel electrode designs for electrochemotherapy, Biochimica et Biophysica Acta, Feb. 11, 1997, 1134, pp. 9-14.
Zlotta, et al, Possible mechanisms fo action of transsurethral needle ablation of the prostate on benign prostatic hyperplasia systems: a neurohistochemical study, Journal of Urology, Mar. 1997, vol. 157, No. 3, pp. 894-899.
Duraiswami et al, Solution of electrical impedance tomography equations using boundary element methods, Boundary Element Technology XII, Apr. 1997, pp. 227-237.
Fox, Nicholls, Sampling conductivity images via MCMC, Auckland University, Auckland, New Zealand, May 1997.
Naslund, Transurethral needle ablation of the prostate, Urology, Aug. 1997, vol. 50, No. 2, pp. 167-172.
Boone, et al, Review imaging with electricity: Report of the European concerted action on impedance tomography, Journal of Medical Engineering & Technology, Nov. 1997, vol. 21, No. 6, pp. 201-232.
Lurquin, Review: Gene transfer by electroporation, Molecular Biotechnology, 1997, vol. 7, pp. 5-31.

(56) References Cited

OTHER PUBLICATIONS

Hapala, Breaking the barrier: methods for reversible permeabilization of cellular membranes, Critical Reviews in Biotechnology, 1997, 17(2), pp. 105-122.

Duraiswami, et al, Boundary element techniques for efficient 2-D and 3-D electrical impedance tomography, Chemical Engineering Science, 1997, vol. 52, No. 13, pp. 2185-2196.

Pinero, et al, Apoptotic and necrotic cell death are both induced by electroporation in HL60 human promyeloid eukaemia cells, Apoptosis, 1997, 2, pp. 330-336.

Miklavcic, et al, The importance of electric field distribution for effective in vivo electroporation of tissues, Biophysical Journal, May 1998, vol. 74, pp. 2152-2158.

Issa, et al, Recent Reports: The TUNA procedure for BPH: Review of the technology, Infections in Urology, Jul. 1998.

Lundqvist, et al, Altering the biochemical state of individual cultured cells and organelles with ultramicroelectrodes, Proc. Natl. Acad. Sci. USA, Sep. 1998, Vo. 95, pp. 10356-10360.

Issa, et al, Specialty Surgery: The TUNA procedure for BPH: Basic procedure and clinical results, Infections in Urology, Sep. 1998.

Dev, et al, Sustained local delivery of heparin to the rabbit arterial wall with an electroporation catheter, Catheterization and Cardiovascular Diagnosis, 1998, 45, pp. 337-345.

Duraiswami, et al, Efficient 2D and3D electrical impedance tomography using dual reciprocity boundary element echniques, Engineering Analysis with Boundary Elements, 1998, 22, pp. 13-31.

Mir, et al, Effective treatment of cutaneous and subcutaneous malignant tumors by electrochemotherapy, 1998, British Journal of Cancer, 77 (12), pp. 2336-2342.

Sersa, et al, Tumor blood flow modifying effect of electrochemotherapy with Bleomycin, Anticancer Research, 1999, 19, pp. 4017-4022.

Thompson, et al, To determine whether the temperature of 2% lignocaine gel affects the initial discomfort which may be associated with its instillation into the male urethra, BJU International, 1999, 84, pp. 1035-1037.

Gumerov, et al, The dipole approximation method and its coupling with the regular boundar yelement method for afficient electrical impedance tomography, BETECH 99, Jun. 1999.

Yang, et al, Dielectric properties of human luekocyte subpopulations determined by electrorotation as a cell separation criterion, Jun. 1999, vol. 76, pp. 3307-3014.

Huang, Rubinsky, Micro-electroporation: improving the efficiency and understanding of electrical permeabilization of cells, Biomedical Microdevices, 1999, 2:2, pp. 145-150.

Mir, Orlowski, Mechanisms of electrochemotherapy, Advanced Drug Delivery Reviews, 1999, 35, pp. 107-118.

Jaroszeski, et al, In vivo gene delivery by electroporationi, Advanced Drug Delivery Reviews, 1999, 35, pp. 131-137.

Gehl, et al, In vivo electroporation of skeletal muscle: threshold, efficacy and relation to electric field distribution, Biochimica et Biophysica Acta, 1999, 1428, pp. 233-240.

Heller, et al, Clinical applications of electrochemotherapy, Advanced Drug Delivery Reviews, 1999, 35, 119-129.

Holder, et al, Low-Frequency System, Assessment and calibration of a low-frequency impedance tomography (EIT), optimized for use in imaging brain function in ambulant human subjects, Annals New York Academy Sciences, pp. 512-519, 1999.

Dev, et al, Medical applications of electroporation, IEEE Transactions on Plasma Science, Feb. 2000, vol. 28, No. 1, pp. 206-222.

Eppich, et al, Pulsed electric fields for seletion of hematopoietic cells and depletion of tumor cell contaminants, gature America, Aug. 2000, vol. 18, pp. 882-887.

Mir, Therapeutic perspectives of in viva cell electropermeabilization, Bioelectrochemistry, 2000, 53, pp. 1-10.

Al-Khadra, et al, The role of electroporation in defibrillation, Circulation Research, Oct. 27, 2000, 87, pp. 797-804.

Miklavcic, et al, A validated model of in vivo electric field distribution in tissues for electrochemotherapy and for DNA alectrotransfer for gene therapy, Biochimica et Biophysica Acta, 2000, 1523, pp. 73-83.

Rubinsky, Cryosurgery, Annu. Rev. Biomed. Eng. 2000, 2, pp. 157-187.

Mir, Orlowski, Introduction: Electropermeabilization as a new drug delivery approach, Methods in Molecular Medicine, 2000, vol. 37, pp. 99-117.

O'Brien, et al, Investigation of the Alamar Blue (resarzurin) fluorescent dye for the assessment of mammalian cell aytotoxicity, Eur J Biochem, 2000, 267, pp. 5421-5426.

Ivanusa, et al, MRI macromolecular contrast agents as indicators of changed tumor blood flow, Radiol Oncol, 2001, 35, 2, pp. 139-147.

Ermolina, et al, Study of normal and malignant white blood cells by time domain dielectric spectroscopy, IEEE Transactions on Dielectrics and Electrical Insulation, Apr. 2001, vol. 8, No. 2, pp. 253-261.

Carson, et al, Improving patient satisfaction, BPH management strategies, Supplement to Urology Times, May 2001, vol. 29, Suppl. 1, pp. 1-22.

Beebe, et al, Nanosecond pulsed electric field (nsPEF) effects on cells and tissues: Apoptosis induction and tumor growth inhibition, IEEE, 2002, pp. 211-215.

Vidamed, When patient satisfaction is your goal, Precision Office TUNA System, VidaMed, Inc., 2001.

Chandrasekar, et al, Transurethral needle ablation of the prostate (TUNA)—A prospective study, six year follow up, pp. 1210, (2001).

Vidamed, Highlights from worldwide clinical studies, Transurethral needle ablation (TUNA), Vidamed's Office TUNA System, VidaMed, Inc. , pp. 1-4, (2001).

Schoenbach, et al, Intracellular effect of ultrashort electrical pulses, Bioelectromagnetics, 2001, 22, pp. 440-448.

Cemazar, et al, Electroporation of human microvascular endothelial cells: evidence for an anti-vascular mechanism of electrochemotherapy, British Journal of Cancer, 2001, 84, 4, pp. 565-570.

Kotnik, et al, Cell membrane electropermeabilization by symmetrical biopolar rectangular pulses, Part I. Increased efficiency of permeabilization, Bioelectrochemistry, 2001, 54, pp. 83-90.

Kotnik, et al, Cell membrane electropermeabilization by symmetrical biopolar rectangular pulses, Part II. Reduced electrolytic contamination, Bioelectrochemistry, 2001, 54, pp. 91-95.

Coates, et al, The electric discharge of the electric eel, Electrophorus electricus (Linnaeus), Zoologica: New York Zoological Society, (Apr. 4, 1937) pp. 1-32.

Lynn, et al, A new method for the generation and use of focused ultrasound in experimental biology, (1942) pp. 179-193.

Neumann, Rosenheck, Permeability changes induced by electric impulses in vesicular membranes, J. Membrane Biol., (1972), 10, pp. 279-290

Crowley, Electrical breakdown of bimolecular lipid membranes as an electromechanical instability, Biophysical Journal, (1973), vol. 13, 711-724.

Zimmermann, et al, Dielectric breakdown of cell membranes, Biophysical Journal, (1974), Vol. 14, pp. 881-899.

Organ, Electrophysiologic principles of radiofrequency lesion making, Appl. Neurophysiol, (1976), 39, pp. 69-76

Kinosita, Jr., Tsong, Hemodialysis of human erythrocytes by a transient electric field, Biochemistry, 1977, vol. 74, No. 5, pp. 1923-1927.

Kinsoita, Jr., Tsong, Formation and resealing of pores of controlled sizes in human erythrocyte membrane, (Aug. 1977), vol. 268, pp. 438-441.

Kinosita, Jr., Tsong, Voltage-induced pore formation and hemolysis of human erythrocytes, Biochimica et Biophysica Acta, (1977), pp. 227-242.

Baker, Knight, Calcium-dependent exocytosis in bovine adrenal medullary cells with leaky plasma membranes, lature, (Dec. 1978), vol. 276, pp. 620-622.

Gauger, Bentrup, A study of dielectric membrane breakdown in the Fucus egg, J. Membrane Biol., (1979), 48, pp. 249-264.

(56) References Cited

OTHER PUBLICATIONS

Erez, Shitzer, Controlled destruction and temperature distributions in biological tissues subjected to monactive electrocoagulation, Transactions of theASME, (Feb. 1980), vol. 102, pp. 42-49.
Neumann, et al, Gene transfer into mouse lyoma cells by electroporation in high electric fields, The EMBO Journal, (1982), vol. 1, No. 7, pp. 841-845.
Seibert, et al, Clonal variation of MCF-7 breast cancer cells in vitro and in athymic nude mice, Cancer Research, (May 1983), 43, pp. 2223-2239.
Brown, Phototherapy of tumors, World J. Surg., (1983), 7, 700-709.
Onik, et al, Ultraonic characteristics of frozen liver, Cryobiology, (1984), 21, pp. 321-328.
Gilbert, et al, The use of ultrsound imaging for monitoring cryosurgery, IEEE Frontiers of Engineering and computing in Health Care, (1984), pp. 107-111.
Onik, et al, Sonographic monitoring of hepatic cryosurgery in an experimental animal model, AJR, (May 1985), 144, pp. 1043-1047.
Griffiths, The importance of phase measurement in e lectrical impedance tomography, Phys. Med. Biol., (Nov. 1987), vol. 32, No. 11, pp. 1435-1444.
Okino, Mohri, Effects of high-voltage electrical impulse and an anticancer drug on in vivo growing tumors, Jpn. J. Cancer Res., (Dec. 1987), 78, pp. 1319-1321.
Kinosita, Jr. et al, Electroporation of cell membrane visualized under a pulsed-laser fluorescence microscope, Biophys. J., (Jun. 1988), vol. 53, pp. 1015-1019.
Amasha, et al, Quantitative assessment of impedance tomography for temperature measurements in microwave hyperthermia, Clin. Phys. Physiol. Meas., (1988), vol. 9, Suppl. A, pp. 49-53.
Asmai, et al, Dielectric properties of mouse lymphocytes and erythrocytes, Biochimica et Biophysica Acta, (1989), 1010, pp. 49-55.
Griffiths, Zhang, A dual-frequency electrical impedance tomography system, Phys. Med. Biol., (1989), vol. 34, No. 10, pp. 1465-1476.
Rowland, et al, Transvenous ablation of atrioventricular conduction with a low energy power source, Br Heart J, (1989), 62, pp. 361-366.
Marsazalek, et al, Schwan equation and transmembrane potential induced by alternating electric field, Biophysical Journal, (Oct. 1990), vol. 58, pp. 1053-1058.
Tekle, et al, Electroporation by using bipolar oscillating electric field: An improved method for DNA transfection of NIH 3T3 cells, Biochemistry, (May 1991), vol. 88, pp. 4230-4234.
Mir, et al, Electrochemotherapy potentiation of antitumour effect of bleomycin by local electric pulses, Eur. J. Cancer, (1991), vol. 27, No. 1, pp. 68-72.
Mir, et al, Electrochemotherapy, a novel antitumor treatment: first clinical trial, Cancerology, (1991), 313, pp. 613-618.
Narayan, Dahiya, Establishment and characterization of a human primay prostatic adenocarcinoma cell line (ND-1_, The Journal of Urology, Nov. (1992) vol. 148, pp. 1600-1604.
Griffiths, et al, Measurement of pharyngeal transit time by electrical impedance tomography, Clin. Phys. Physiol. Meas., (1993), vol. 13, Suppl. A, pp. 197-200.
Rols, et al, Highly efficient transfection of mammalian cells by electric field pulses application to large vols. Of cell culture by using a flow system, Eur. J. Biochem., (1992), 205, pp. 115-121.
Brown, et al, Blood flow imaging using electrical impedance tomography, Clin. Phys. Physiol. Meas., (1992), 13, Suppl. A, pp. 175-179.
Foster, et al, Production of prostatic lesions in canines usign transrectally administered high-intensity focused ultrasound, Eur Urol, (1993), pp. 330-336.
Shiina, et al, Percutaneous ethanol injection therapy for hepatocellular carcinoma: Results in 146 patients, AJR, (May 1993), 160, pp. 1023-1028.

Salford, et al, A new brain tumour therapy combining bleomycin with in vivo electropermeabilization, Biochemical and Biohysical Research Communications, (Jul. 30, 1993), vol. 194, No. pp. 938-943.
Glidewell, NG, The use of magnetic resonance imaging data and the inclusion of anisotropic regions in electrical Impedance tomography, ISA, (1993), pp. 251-257.
Gascoyne, et al, Membrane changes accompanying the induced differentiation of Friend murine erythroleukemia ells studied by dielectrophoresis, Biochimca et Biophysica Acta, (1993), 1149, pp. 119-126.
Foster, et al, High-intensity focused ultrsound in the treatment of prostatic disease, Eur Urol, (1993), 23(suppl1), pp. 29-33.
Andreason, Electroporation as a technique for the ransfer of macromolecules into mamalian cell lines, J. Tiss. Cult. Meth., (1993), 15, pp. 56-62.
Weaver, Electroporation: A general phenomenon for manipulating cells and tissues, Journal of Cellular Biochemistry, (1993), 51, pp. 426-435.
Barber, Electrical impedance tomography applied potential tomography, Advances in Biomedical Engineering, (1993), IOS Press, pp. 165-173.
Cook, et al, ACT3: a high-speed, high-precision electrical impedance tomograph, IEEE Transactions on Biomedical Engineering, (1994), vol. 41, No. 8, pp. 713-722.
Alberts, et al, Molecular biology of the Cell, Biocchemical education, (1994), 22(3), pp. 164.
Hughes, et al, An analysis of studies comparing electrical impedance tomography with x-ray videofluoroscopy in the assessment of swallowing, Physiol. Meas. (1994), 15, pp. A199-A209.
Mazurek, et al, Effect of Short HV Pulses in Bacteria and Fungi, (1995), vol. 2, No. 3, pp. 418-425.
Griffiths, Tissue spectroscopy with electrical impedance tomography: Computer simulations, IEEE Transactions on Biomedical Engineering, Saep (1995), vol. 42, No. 9, pp. 948-954.
Gencer, et al, Electrical impedance tomography: Induced-currentimaging achieved with a multiple coil system, IEEE Transactions on Biomedical Engineering, (Feb. 1996), vol. 43, No. 2, pp. 139-149.
Weaver, Chizmadzhev, Theory of electroporation: a review, Biolectrochemistry and Bioenergetics, (1996), vol. 41, pp. 135-160.
Gimsa, et al, Dielectric spectroscopy of single human erythrocytes at physiological ionic strength: Dispersion of the aytoplasm, Biophysical Journal, (Jul. 1996), vol. 71, pp. 495-506.
Hall, et al, Nanosecond pulsed electric fields induce apoptosis in p53-wildtype and p53-null HCT116 colon carcinoma mils, Apoptosis, May 23, 2007, 12, pp. 1721-1731.
Sel, et al, Feasibility of employing model-based optimization of pulse amplitude and electrode distance for effective tumor electropereabilization, IEEE Transactions on Biomedical Engineering, May 2007, vol. 54, No. 5, pp. 773-781.
Kirson, et al, Alternating electric fields arrest cell proliferation in animal tumor models and human brain tumor, PNAS, Jun. 12, 2007, vol. 104, No. 24, pp. 10152-10157.
Talele, Gaynor, Non-linear time domain model of electropermeabilizationi: Response of a single cell to an arbitary applied electric field, Journal of Electrostatics, Jul. 16, 2007, 65, pp. 775-784.
Esser, et al, Towards solid tumor treatment by irreversible electroporation: Intrinsic redistribution of fields and aurrents in tissue, Technology in Cancer Research and Treatment, Aug. 2007, vol. 6, No. 4, pp. 261-273.
Maor, et al, The effect of irreversible electroporation on blood vessels, Technology in Cancer Research and Treatment, Aug. 2007, vol. 6, No. 4, pp. 307-312.
Edd, Davalos, Mathematical modeling of irreversible electroporation for treatment planning, Technology in Cancer Research and Treatment, Aug. 2007, vol. 6, No. 4, pp. 275-286.
Rubinsky, Irreversible electroporation in medicine, Technology in Cancer Research and Treatment, Aug. 2007, vol. 3, No. 4, pp. 255-259.

(56) References Cited

OTHER PUBLICATIONS

Onik, et al, Irreversible electroporation: Implications for prostate ablation, Technology in Cancer Research and Treatment, Aug. 2007, vol. 6, No. 4, pp. 295-300.
Lee, et al, Imaging guided percutaneous irreversible electroporation: Ultrasound and immunohistological correlation, Technology in Cancer Research and Treatment, Aug. 2007, vol. 6, No. 4, pp. 287-293.
Bertacchini, et al, Design of an irreversible electroporation system for clinical use, Technology in Cancer Research and Treatment, Aug. 2007, vol. 6, No. 4, pp. 313-320.
Al-Sakere, et al, A study of the immunological response to tumor ablation with irreversible electroporation, Technology in Cancer Research and Treatment, Aug. 2007, vol. 6, No. 4, pp. 301-305.
Fischbach, et al, Engineering tumors with 3D scaffolds, Nature Methods, Sep. 2, 2007, vol. 4, No. 10, pp. 855-860.
Ivorra, Rubinsky, In vivo electrical impedance measurements during and after electroporation of rat liver, Bioelectrochemistry, Oct. 21, 2007, 70, pp. 287-295.
Yao, et al, Study of transmembrane potentials of inner and outer membranes induced by pulsed-electric-field model and simulation, IEEE Transactions on Plasma Science, Oct. 2007, vol. 35, No. 5, pp. 1541-1549.
Corovic, et al, Analytical and numerical quantification and comparison of the local electric field in the tissue for different electrode configurations, BioMedical Engineering Online, Oct. 15, 2007, 6, 37, pp. 1-14.
Schoenbach, et al, Bioelectric effects of intense nanosecond pulses, IEEE Transactions on Dielectric and Electrical Insulation, 2007, vol. 14, Iss. 5, pp. 1088-1109.
Al-Sakere, et al, Tumor ablation with irreversible electroporation, PLOS One, Nov. 7, 2007, Iss. 11, el135, pp. 1-8.
Hall, et al, Nanosecond pulsed electric fields have differential effects on cells in the S-phase, DNA and Cell Biology, 2007, vol. 26, No. 3, pp. 160-171.
He, et al, Nonlinear current response of micro electroporation and resealing dynamics for human cancer cells, Bioelectrochemistry, Jan. 29, 2008, 72, pp. 161-168.
Ott, et al, Perfusion-decellarized matrix: using nature's platform to engineer a bioartificial heart, Nature Medicine, Jan. 13, 2008, vol. 14, No. 2, pp. 213-221.
Ron, et al, Cell-based screening for membranal and cytoplasmatic markers using dielectric spectroscopy, Biophysical chemistry, Mar. 29, 2008, 135, pp. 59-68.
Garcia, et al, Irreversible electroporation (IRE) to treat brain tumors, Proceedings of the ASME 2008 Summer Bioengineering Conference (SBC2008), Jun. 25, 2008, pp. 6-7.
Davalos, Rubinsky, Temperature considerations during irreversible electroporation, International Journal of Heat and Mass Transfer, Jun. 14, 2008, 51, pp. 5617-5622.
Dahl, et al, Nuclear shape, mechanics and mechanotransduction, Circulation Research, Jun. 6, 2008, 102, pp. 1307-1318.
Seidler, et al, A Cre-loxP-based mouse model for conditional somatic gene expression and knockdown in vivo by using avian retroviral vectors, PNAS, Jul. 22, 2008, vol. 105, No. 29, pp. 10137-10142.
Maor, et al, Intravascular irreversible electroporation: Theoretical and experimental feasibility study, 30th Annual International IEEE EMBS Conference, IEEE, Aug. 20, 2008, pp. 2051-2054.
Maor, et al, Irreversible electroporation attenuates neointimal formation after angioplasty, IEEE Transactions on Biomedical Engineering, Sep. 2008, vol. 55, No. 9, pp. 2268-2274.
Jensen, et al, Tumor volume in subcutaneous mouse xenografts measured by microCT is more accurate and reproducible than determined by 18F-FDG-microPET or external caliper, BMC Medical Imaging, Oct. 16, 2008, 8, 16,m pp. 1-9.
Rubinsky, et al, Optimal parameters for the destruction of prostate cancer using irreversible electroporation, The Journal of Urology, Dec. 2008, vol. 180, pp. 2668-2674.
Daud, et al, Phase I trial of Interleukin-12 plasmid electroporation in patients with metastatic melanoma, Journal of Clinical Oncology, Dec. 20, 2008, vol. 26, No. 36, pp. 5896-5903.
Flanagan, et al, Unique dielectric properties distinguish stem cells and their differentiated progeny, Stem Cells, 2008, 26, pp. 656-665.
Mali, et al, the effect of electroporation pulses on functioning of the heart, Med Biol Eng Comput, 2008.
Kuthi, Gundersen, Nanosecond uplse generator with scalable pulse amplitude, IEEE, 2008, pp. 65-68.
Craiu, Scadden, Chapter 22 flow electroporation with pulsed electric fields for purging tumor cells, Electroporation Protocols: Preclinical and Clinical Gene Medicine, Methods in Molecular Biology, vol. 423, pp. 301-310 (2008).
Mir, Chapter 1 application of electroporation gene therapy: Past, current and future, Electroporation Protocols: Preclinical and Clinical Gene Medicine, Methods in Molecular Biology, vol. 423, pp. 3-17 (2008).
Lin, Lee, An optically induced cell lysis device using dielectrophoresis, Applied Physics Letters, Jan. 20, 2009, 94, 033901, pp. 1-3.
Kroeger, et al, Curvature-driven pore growth in charged membranes during charge-pulse and voltage-clamp experiments, Biophysical Journal, Feb. 2009, 96, 3, pp. 907-916.
Maor, et al, Non thermal irreversible electroporation: Novel technology for vascular smooth muscle cells abation, Plos One, Mar. 9, 2009, vol. 4757-, Iss. 3, e4757, pp. 1-9.
Shafiee, et al, A preliminary study to delineate irreversible electroporation from thermal damage using the Arrhenius equation, Journal of Biomedical Engineering, Jul. 2009, vol. 131, 074509, pp. 1-5.
Granot, et al, In vivo imaging of irreversible electroporation by means of electrical impedance tomography, Phys. Med. Biol., Jul. 30, 2009, 54, pp. 4927-4943.
Daniels, Rubinsky, Electrical field and temperature model of nonthermal irreversible electroporation in heterogeneous tissues, Journal of Biomedical Engineering, Jul. 2009, vol. 131, 071006, pp. 1-12.
Esser, et al, Towards solid tumor treatment by nanosecond pulsed electric fields, Technology in Cancer Research and Treatment, Aug. 2009, vol. 8, No. 4, pp. 289-306.
Ivorra, et al, In vivo electrical conductivity measurements during and after tumor electroporation: conductivity ahanges reflect the treatment,Phys. Med. Biol., Sep. 17, 2009, 54, pp. 5949-5963.
Garcia, et al, Pilot study of irreversible electroporation for intracranial surgery, 31st Annual International Conference of the IEEE EMBS, IEEE, Sep. 2, 2009, pp. 6513-6516.
Hong, et al, Cardiac ablation via electroporation, 31st Annual International Conference of the IEEE EMBS, IEEE, Sep. 2, 2009, pp. 3381-3384.
Neal, Davalos, The feasibility of irreversible electroporation for the treatment of breast cancer and other heterogeneous systems, Annals of Biomedical Engineering, Dec. 2009, vol. 37, No. 12, pp. 2615-2625.
Sharma, et al, Review on thermal energy storage with phase change materials and applications, Renewable and Sustainable Energy Reviews, 2009, 13, pp. 318-345.
Ibey, et al, Selective cytotoxicity of intense nanosecond-duration electric pulses in mammalian cells, Biochim Biophys Acta, Nov. 2010, 1800, 11, pp. 1210-1219.
Tsivian, Polascik, Recent advances in focal therapy of prostate and kidney cancer, Medicine Reports, Jan. 18, 2010, 2, 1, pp. 1-3.

* cited by examiner

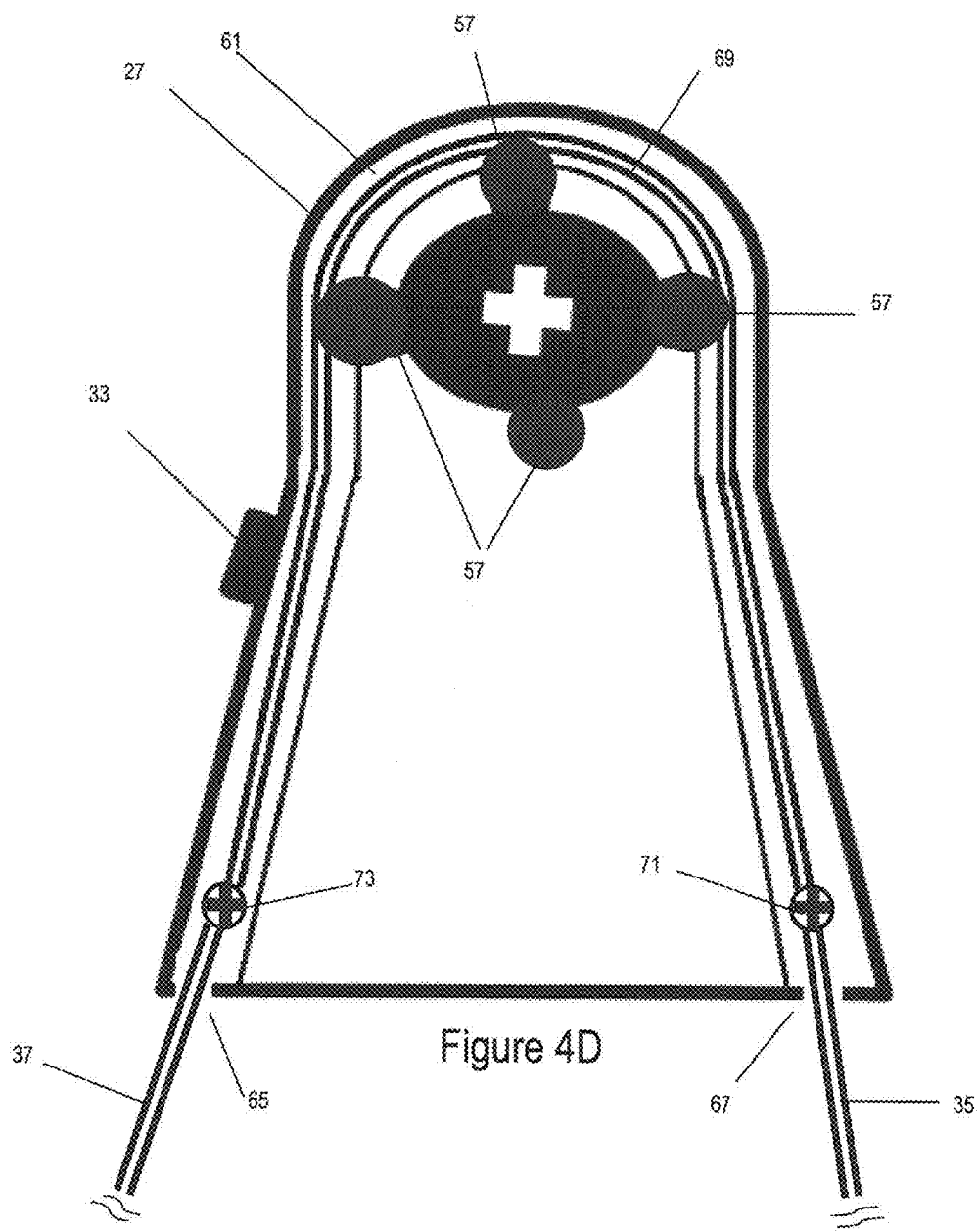

INTEGRATED PUMP AND GENERATOR DEVICE AND METHOD OF USE

CROSS REFERENCE TO RELATED APPLICATIONS

This application is related to U.S. provisional patent application Ser. No. 61/755,426 entitled "Modular Ablation System and Fluid Pump for Same", filed Jan. 22, 2013; U.S. provisional patent application Ser. No. 61/771,574, entitled "Modular Ablation System and Graphical User Interface for Same", filed Mar. 1, 2013; and U.S. provisional patent application Ser. No. 61/824,843 entitled "Modular Ablation System and Graphical User Interface for Same", filed May 17, 2013, which are incorporated herein by reference.

FIELD OF THE INVENTION

The invention relates generally to devices and methods that may be used in therapeutic or ablative tissue treatment applications. More particularly, the invention relates to devices and methods for regulating, maintaining, and/or controlling delivery of fluids during the use in such applications.

BACKGROUND

Ablation technology such as radiofrequency (RF), microwave, and irreversible electroporation (IRE), both thermal IRE and non-thermal IRE, are well known for their applicability in the treatment, coagulation, or targeted ablation of tissue. During such procedures, the electrode or antenna of an ablation probe of the monopole, dipole, or helical variety, as is conventional in the art, is typically advanced into the patient either laparoscopically or percutaneously until the target tissue is reached.

Following the introduction of the ablation probe, during the transmission of treatment energy to the target tissue, the outer surface of the probe may sometimes reach unnecessarily high temperatures due to ohmic or ionic heating, specifically when the treatment energy is in the form of either RF or microwave. When exposed to such temperatures, the treatment site, as well as the surrounding tissue, may be unintentionally heated beyond the desired treatment parameters or treatment zone. In order to prevent such unintentional heating cooling fluid may be infused or pumped through the ablation system. Additionally, the cooling fluid may also be used to cool the ablation device itself to prevent unintended device damage or harm to the user or patient. Infusion ablation devices fluid, such as saline, may also be used to improve conductivity during the ablation procedure to allow for faster procedure times and larger treatment zones. Additionally, in the case of IRE, unwanted rises in tissue temperature may occur in tissue directly adjacent to the electrodes. The present disclosure discloses restricting such unwanted effects by providing improved ablation treatment devices with integrated fluid delivery systems and methods of use.

The integrated fluid delivery system of this disclosure may be used for delivery of more than just cooling fluids. For example, during IRE treatment is may be necessary to deliver nanoparticles, as described in U.S. Pat. No. 8,465,484 (which is hereby incorporated by reference) and materials for tissue regeneration, as described in U.S. Pat. No. 8,231,603 (which is hereby incorporated by reference).

SUMMARY OF THE INVENTION

There is a need in the art for an improved fluid delivery system used with ablation technologies that is inexpensive to manufacture, easy to use, and is reliable.

The present disclosure is directed to an improved fluid delivery system used with ablation technologies for the treatment or ablation of tissue. In one embodiment the device includes a multiple-use subassembly having housing having an energy source and a pump motor, and a single-use subassembly having a pump head, fluid source, and an ablation probe.

DESCRIPTION OF THE DRAWINGS

FIG. 4A-4E are partial cross-sectional views of a pump head.

DETAILED EMBODIMENTS

The present invention can be understood more readily by reference to the following detailed description and the examples included therein and to the figures. The figures, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology user herein is for the purpose of describing particular embodiments only and is not intended to be limiting.

As used herein, the term "proximal" denotes the direction closer to the operator and the term "distal" denotes the direction closer to the patient.

The invention described herein is for a new and useful fluid delivery system that may be integrated into an ablation system. Such ablation systems may include an RF ablation system, a microwave ablation system, and an IRE ablation system. An ablation system, including an RF, microwave, and IRE system, typically includes a generator or power source, a probe consisting of at least one electrode, antenna, or other energy transmitting source, wires to connect the power source with the energy transmitting source, and a fluid delivery system. The purpose of the fluid delivery system may include, but is not limited to, delivering cooling fluid, such as saline, to the probe and/or treatment site to prevent unintended, unintentional, or unwanted heating of healthy tissue, probe or energy transmission lines. Another reason for a fluid delivery system may be for delivering fluids other than cooling fluids, including, but not limited to, saline, nanoparticles, chemotherapeutic drugs and materials for tissue regeneration.

Figure 1:
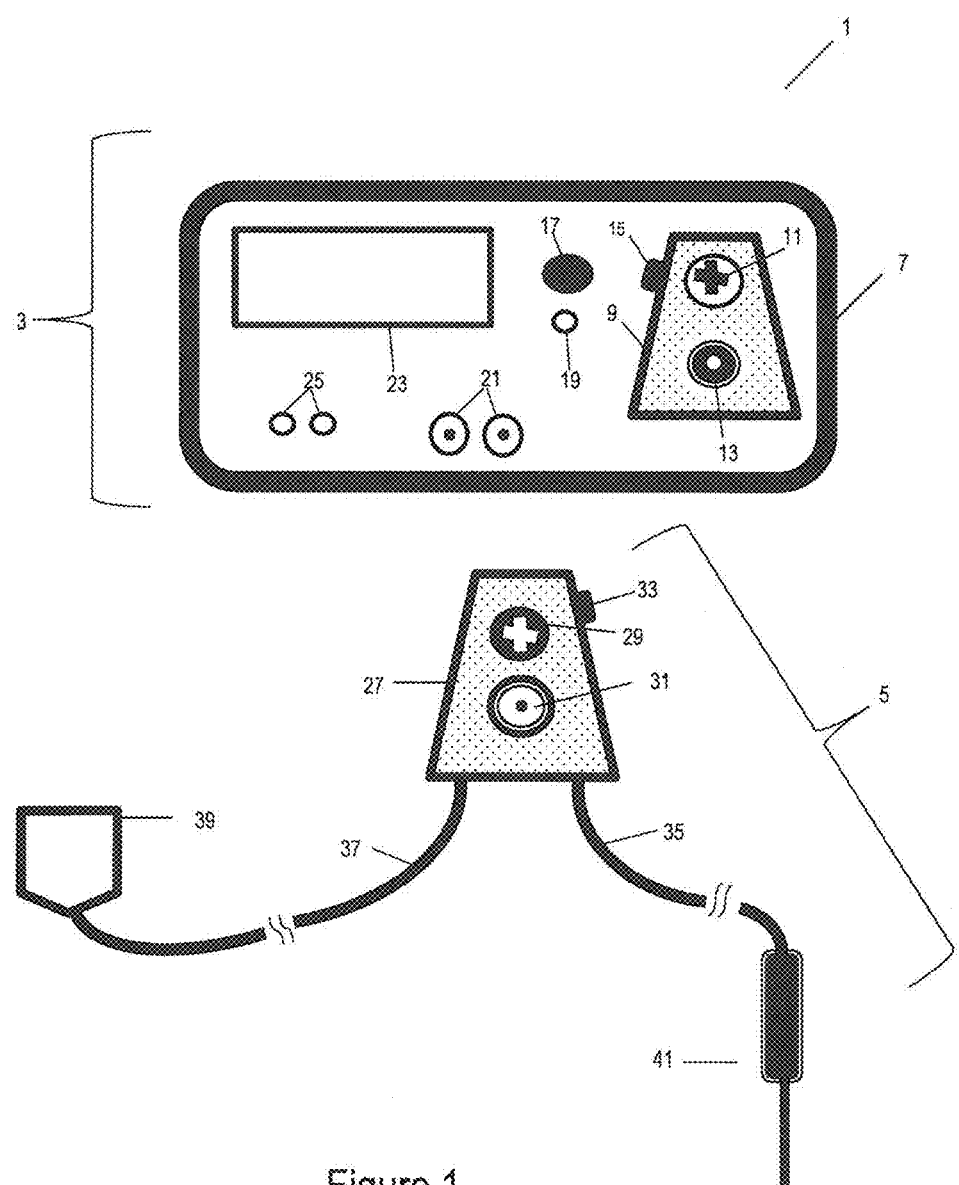
FIG. 1 is a partial front view of the system having a multiple-use subassembly and a single-use subassembly.
Figure 2:
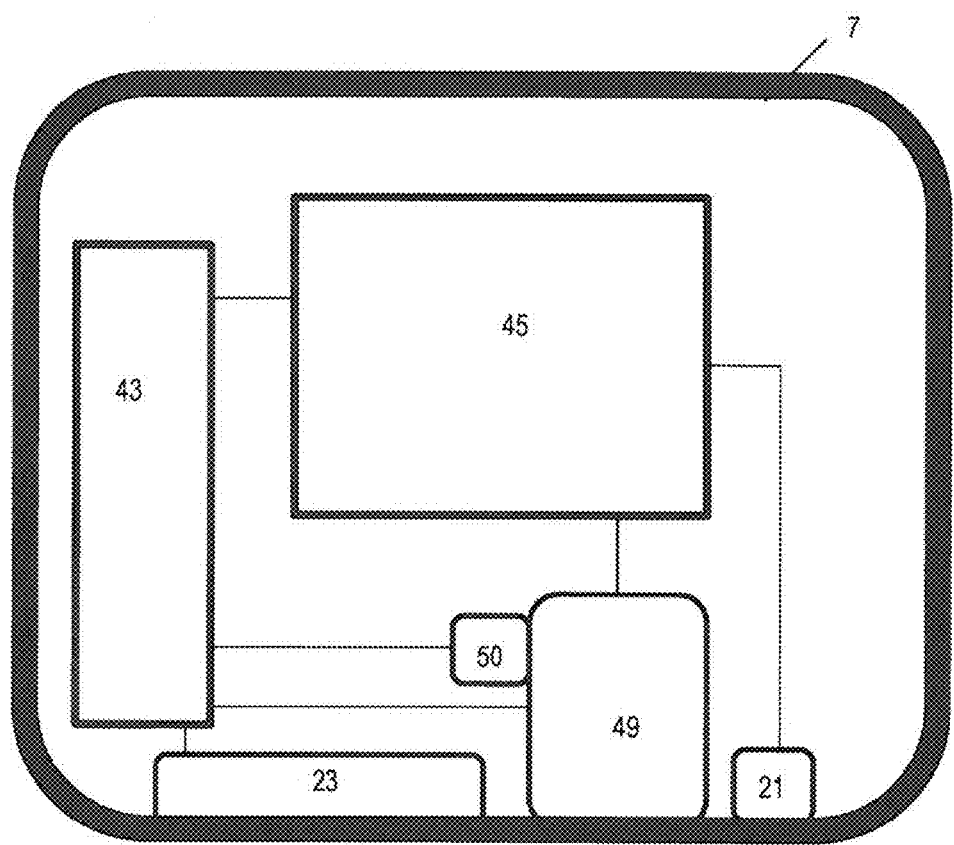
FIG. 2 is a partial top cross-section schematic view of the housing.
Figure 3A:
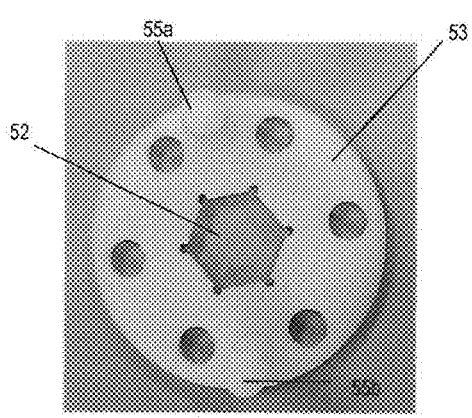
FIG. 3A is a top view of a partially assembled rotor.
Figure 3B:
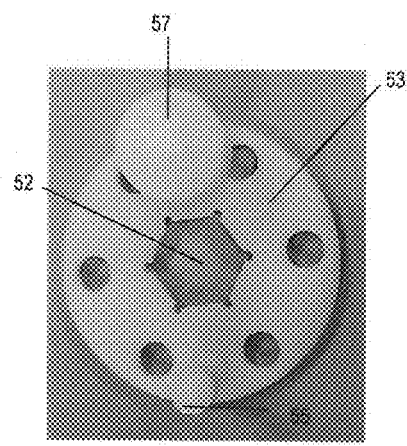
FIG. 3B is a top view of a partially assembled rotor.
Figure 3C:
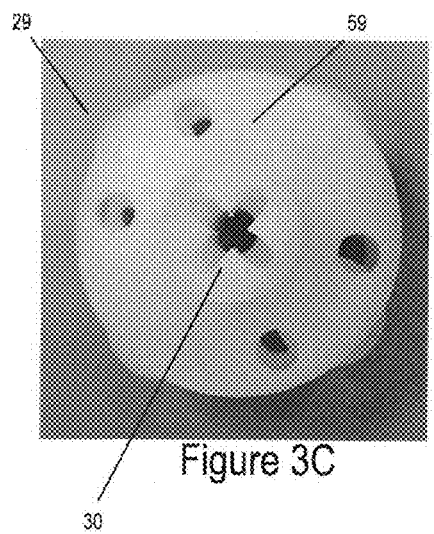
FIG. 3C is a top view of am assembled rotor.
Figure 3D:
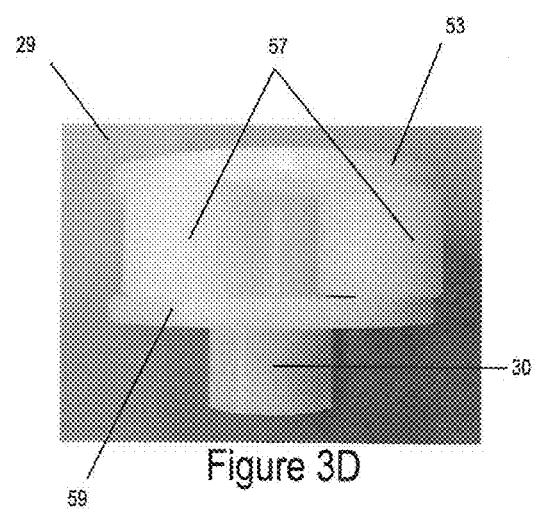
FIG. 3D is a side view of an assembled rotor.

As seen in FIGS. 1-2, the system 1 may comprise of a multiple-use subassembly 3 and a single-use disposable subassembly 5. The multiple-use subassembly 3 may be comprised of a housing 7, a power button 17, a user interface screen 23, grounding pad connection points 25, electrical or probe connection points 21, a power indicator 19, a pump face plate 9, a securement keyhole 15, a drive shaft 11, a pump motor 49 and energy source 45 (as seen in FIG. 2) and in some embodiments, such as the embodiment as shown in FIG. 1, the face plate 9 may also comprise an additional microwave electrical connection point 13. Additionally, if the system is to be used with IRE procedures then the multiple-use subassembly 3 may also include a set of high voltage electrical connectors (not shown) intended to electrically connect the IRE probe to the energy source. The single-use subassembly 5 may comprise of a disposable pump head 27, a securement latch 33, a rotor 29, a fluid source line 37, a probe fluid line 35, and an ablation probe 41. Additionally, the fluid source line 37 may also be in fluid communication with a fluid source 39, such as a saline bag or other fluid container. In some embodiments, such as the embodiment as shown in FIG. 1, the pump head 27 may further comprise of a microwave electrical connection point 31.

Some advantages of integrating the fluid delivery system together with the ablation system include, but are not limited to, creating a device with a smaller footprint and takes up less space in procedure room, a more reliable and robust pump design, a simplified pump assembly to decrease preparation time and possible user error when setting up the pump system, a quick change maintenance system that provides for faster pump motor maintenance, and pre-manufactured fluid tubing sets specific to the type of device being used. Additionally, the single-use subassembly 5 may comprise of the majority of the moving parts for pump thereby reducing the potential for mechanical problems or breakdown of the multi-use components.

For example, a key advantage to the disclosed invention is simplifying user setup and reducing possible errors by the user because the user may not need to do any pump assembly or prepping of pump tubing. The disposable pump head may be fully assembled by manufactured. The user may be able to order a specific pump head that is intended to be used for a specific ablation procedure. Therefore, the pump head may be manufactured with the desired tubing pre-loaded and pre-connected, so all the user needs to do is attached the disposable pump head together with the pump face plate, as described in more detail below.

The housing 7 may be made of metal or other suitable material capable of withstanding repeated and multiple uses, normal wear and tear, and may be easily cleaned. The user interface screen 23 may be a touch screen computer that displays the GUI operating system designed to help guide the user through preparing and operation of the system 1. The connection points 25 may be used to electrically connect grounding pads (not shown), as known in the art. The power indicator 19 may comprise of an LED or visual identification source to indicate to user that power has been activated to system 1. The face plate 9 may be shaped to correspond with and align together with the shape of the pump head 27.

The securement keyhole 15 is designed and shaped so the securement latch 33 of the disposable pump head 27 may align and fit inside of the keyhole 15. This design is intended to ensure that the pump head 27 may be securely attached to the face plate 9 during use and easily removed thereafter. An advantage of using a latch 33 and corresponding keyhole 15 as a securement means is the user may easily secure and release pump head 27 from face plate 9 with one hand. As described in more detail below, the securement latch 33 may be comprised of a button that when depressed may move the securement latch 33. When the securement latch 33 is being depressed by user the latch 33 may freely slide in and out of the securement keyhole 15 without any friction, interference or catching. When the user is not pressing on the latch 33 the latch 33 may continue to freely slide into the securement keyhole 15, however an interference fit with keyhole 15 may be created when user tries to remove latch 33 from the keyhole 15, thereby securely attaching the latch 33 inside of the securement keyhole 15. In FIG. 1, only one keyhole 15 and securement latch 33 is shown, however it is conceivable that multiple securement latches (not shown) and multiple keyholes (not shown) may be used to secure the pump head 27 to the face plate 9. In other embodiments, in place of a latch 33 and keyhole 15 design the pump head 27 may be securely attached to the face plate 9 by a side lever (not shown) to releasably lock pump head 27 in place, a pull tab (not shown); or a tongue and groove type connection to rotate pump head 27 relative to face plate 9.

The drive shaft 11 may be connected to the pump motor 49, as known in the art. The drive shaft 11 may be shaped so it aligns with the rotor 29 of the pump head 27, as described in more detail below. The drive shaft 11 is intended to rotate at speeds capable of generating flow rates ranging from 0.05 mL/min.-100 mL/min. Specific flow rates will depend on the specific ablation devices used and the procedure type. Commonly, devices that require diffusion of fluid into the target tissue, such as RE or IRE probes, use slower flow rates with multiple modes of operation. Devices that require cooling fluid to be cycled through the device typically require higher flow rates. Because this system is conceived to be used with multiple types of ablation technologies the pump is therefore capable of producing a wide range of flow rates. The different flow rates and number of rotations per second of the drive shaft 11 may be controlled by the user interface 23.

The pump head 27 is intended to be disposable and single-use only. The pump head 27 may be made of any disposable material including, but not limited to, plastics or metals. In one embodiment, the pump head 27 may comprise a microwave electrical connection 31 that aligns with and connects with a corresponding microwave electrical connection 13 of the face plate 9. These electrical connections 31, 13 are known in the art and may be any suitable electrical connection capable of transferring electrical energy, such as microwave energy. However, it is also conceived that the electrical connection 31, 13 may be capable of transferring both microwave and radiofrequency energy. An advantage of placing the electrical connections 31, 13 on the disposable pump head 27 and face plate 9 it that the cable transferring microwave energy from generator to probe may become hot during use and therefore need to be cooled by the cooling fluid lines. Alternatively, the electrical connections 31, 13 may not be placed on the disposable pump head 27 and face plate 9; rather they may be placed on the housing 7. In such an embodiment, the cooling fluid lines may also need to be diverted to surround the microwave energy cable. In yet another embodiment, and as shown in FIG. 1, the housing 7 may include additional connection points 21 used to electrically connect a probe, such as a radio frequency probe or IRE probes that may require a pin type connection as known in the art. The pump head 27 may also include a circuit board (not shown) that is intended to store certain information that may be transferred or read by a circuit board inside the housing 7, as described in more detail below.

The type of ablation probe 41 that will be used with single-use subassembly 5 may depend on the type of procedure being performed. The system 1 is capable of generating electrical energy and therefore it is conceivable that various electrical ablation technologies may be used together with this system, including, but not limited to, microwave ablation, radio frequency ablation, or irreversible electroporation. By way of example only, the type of probes that may be used with this system include, but are not limited to, the following devices all manufactured by Angio-Dynaimcs, Inc. (Latham, N.Y.): StarBurst® XL RFA probe; StarBurst® Semi-Flex RFA probe; StarBurst® Xli-enhanced and Semi-Flex RFA probes; StarBurst® MRI RFA probes; StarBurst® SDE RFA probes; StarBurst® Talon and Talon Semi-Flex RFA probes; Acculis® microwave applicators; and NanoKnife® IRE probes.

The invention described herein may have multiple embodiments. Each ablation technology, such as RF, microwave, or IRE, may require a unique or dedicated electrical connection point, however it is conceived that the invention may be able to have a universal electrical connection point. For example, the first embodiment may comprise an RF ablation system with an integrated fluid delivery system having a standard RF pin-type electrical connection 21. The second embodiment may comprise a microwave ablation system with an integrated fluid delivery system having a dedicated microwave electrical connection point 31. The third embodiment may include an IRE ablation system with an integrated fluid delivery system with a dedicated high voltage electrical connection point (not shown). A fourth embodiment may include an ablation system capable of delivering various electrical ablation technologies including, but not limited to, RF pin-type 21, microwave connection 31, and/or IRE (not shown), together with a single integrated fluid delivery system and single energy connection point. A fifth embodiment may include a microwave and RF ablation system with an integrated fluid delivery system having a universal electrical connection point (not shown) capable of transmitting both RF and microwave energy to selected ablation probe.

Referring now to FIG. 2, a schematic top cross-section view of the housing 7 is depicted. The housing 7 may comprise of a power source 43, an energy generator 45, a pump motor 49, a circuit board 50, an electrical connector 21, and a tablet or screen 23 for the user interface. The power source 43 is connected to a power cord (not shown) and is capable of generating the power required to run the entire system 1, including the interface screen 23, the motor 49, the circuit board 50, and the ablation probe 41. In one embodiment, the energy generator 45 may be capable of creating the electrical energy required for microwave ablations, radiofrequency ablations, and irreversible electroporation ablations. Alternately, in various other embodiments the system 1 may only be used for a single type of ablation, such as microwave, RF, or IRE only, and therefore the energy generator 45 may only be required to generator that specific type of energy. The energy generator 45 may transfer energy to the electrical connections 13 (as seen in FIG. 1) of the pump head 49 or electrical connections 21.

The pump motor 49 may be securely attached to front of housing 7 so that the drive shaft 11 extends beyond the face plate 9. The pump motor 49 may be any stepper motor, brushed motor, or brushless motor as known in the art. In one embodiment, the pump motor 49 may be a stepper motor that is directly connected to the drive shaft 11. Alternatively, if a brushed or brushless motor (not shown) is used then such a motor would be connected to a gear box (not shown) which in turn would be connected to the drive shaft 11. Attached to the pump motor 49 may further comprise a circuit board 50. The purpose of the circuit board 50 is to communicate with a corresponding circuit board (not shown) in the pump head 27. The circuit board 50 could be used to communicate information about the pump head 27 including, but not limited to, unique probe serial numbers to prevent counterfeiting or reuse, information about corresponding thermocouplers, date of manufacture, procedure data, expiration dates of probes, and revisions to software and/or probe lifespans. For example, when user connects the pump head 27 to the face plate 9 the information stored on pump head 27 circuit board (not shown) may be transferred to circuit board 50 located in housing 7. Depending on the specific information being transferred the software controlling the interface may automatically set preprogrammed treatment parameters including, but not limited to, specific power settings, algorithms, and flow rates.

Referring now to FIG. 3A-4C, one embodiment of the rotor 29 and pump head 27 are shown. As seen in FIG. 3A-3D, the rotor 29 may comprise of a back plate 53, a front plate 59, connecting arms 55a, 55b, rollers 57, and an alignment knob 30. The rotor 29 may be securely placed inside the pump head 27 (as shown in FIG. 4B). The back plate 53 further comprises a center hole 52. The center hole 52 may be sized so that the back plate 53 may easily be fit over the center axle 63, as seen in FIG. 4A. The connection arms 55a, 55b may function as axles for the rollers 57. One side of the connection arms 55a, 55b may be securely connected to back plate 53 by conventional techniques known in the art, including, but not limited to, a press fit, welding, adhesive, or an interference fit. After the connection arms 55a, 55b are securely attached to the back plate 53, rollers 57 may be slid over the connection arms 55a, 55b. The number of rollers 57 may range from two rollers up to 6 rollers. After the rollers 57 have been placed on the connection arms 55a, 55b the front plate 59 may then be securely attached to the opposite side of connection arms 55a, 55b as shown in FIG. 3C. The front plate 59 may also comprise the alignment knob 30 which is shaped to align and securely attach to the drive shaft 11. The alignment knob 30 may comprise of various shapes and sizes which are intended to correspond and align with matching shaped drive shafts, thereby allowing for easy alignment when user secures pump head 27 to face plate 9. In the embodiment shown here, the alignment knob 30 has a cross or "X" shaped hole where a corresponding cross or "X" shaped drive shaft 11 (as seen in FIG. 1) may fit inside thereof. Other alignment embodiments are also conceived such as using a sprag-clutch (not shown) or other one-way bearings as known in art the to secure the rotor to the drive shaft 11.

Figure 4A:
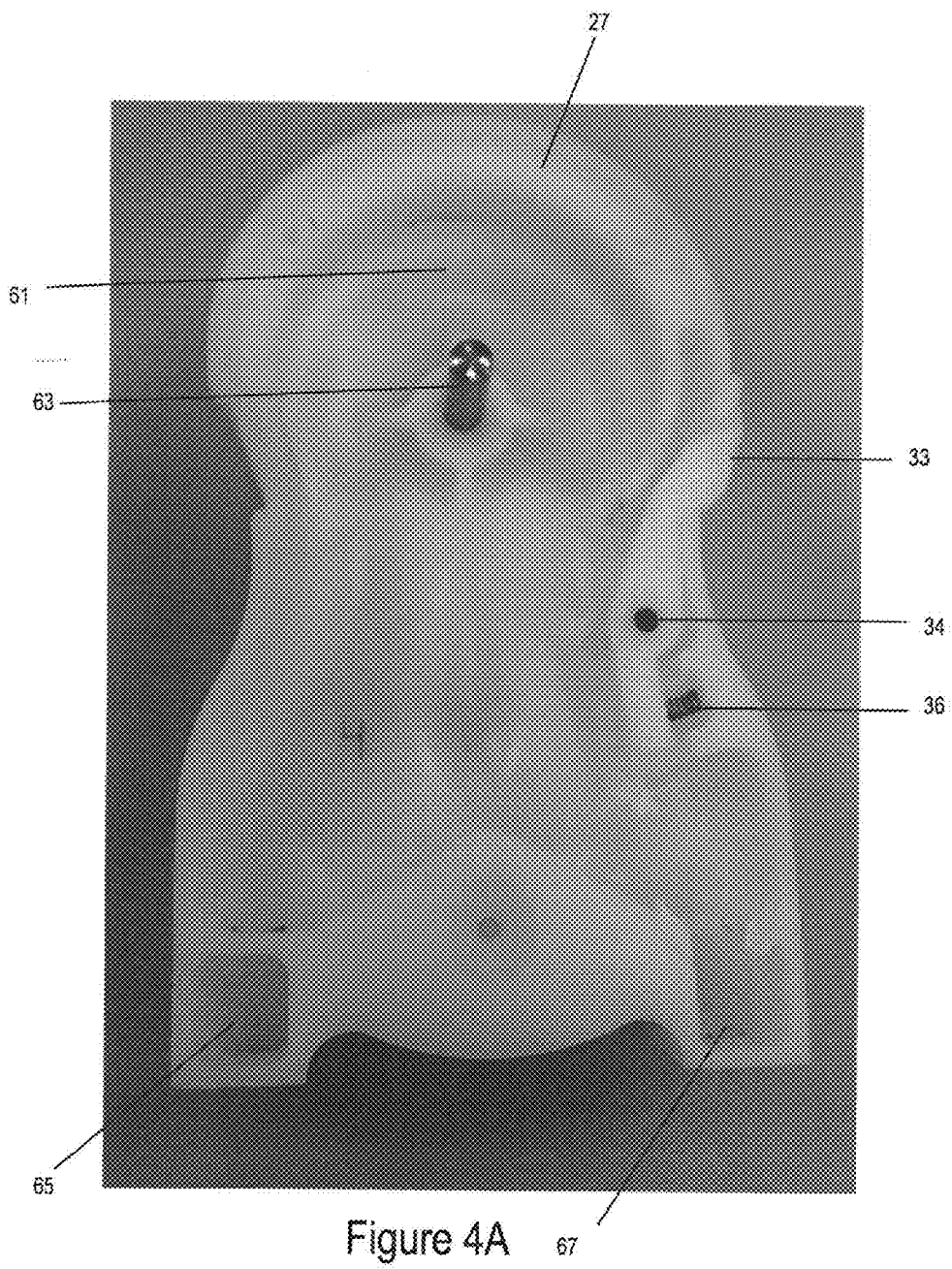

As seen in FIG. 4A, the pump head 27 is shown without the rotor 29 assembly attached. The pump head 27 may further comprise a tubing track 61, an axle 63, the securement latch 33, a securement hinge pin 34, a securement spring 36, a first tubing line port 65, a second tubing line port 67, and a back plate (not show). The axle 63 may be metal or other suitable material that is securely attached to the pump head 27. The tubing track is designed to provide a space for the peristaltic tubing to be placed. The securement latch 33 may be a button that when pushed down or depressed toward the pump head 27 by user causes the latch 34 to hinge along the hinge pin 34 and rotate thereby pushing up against the spring 36. When user releases the securement latch 33 the spring 36 forces latch 33 to hinge away from the pump head 27. The first and second tubing ports 65, 67 provide areas for tubing to extend through the pump head 27.

Figure 4B:
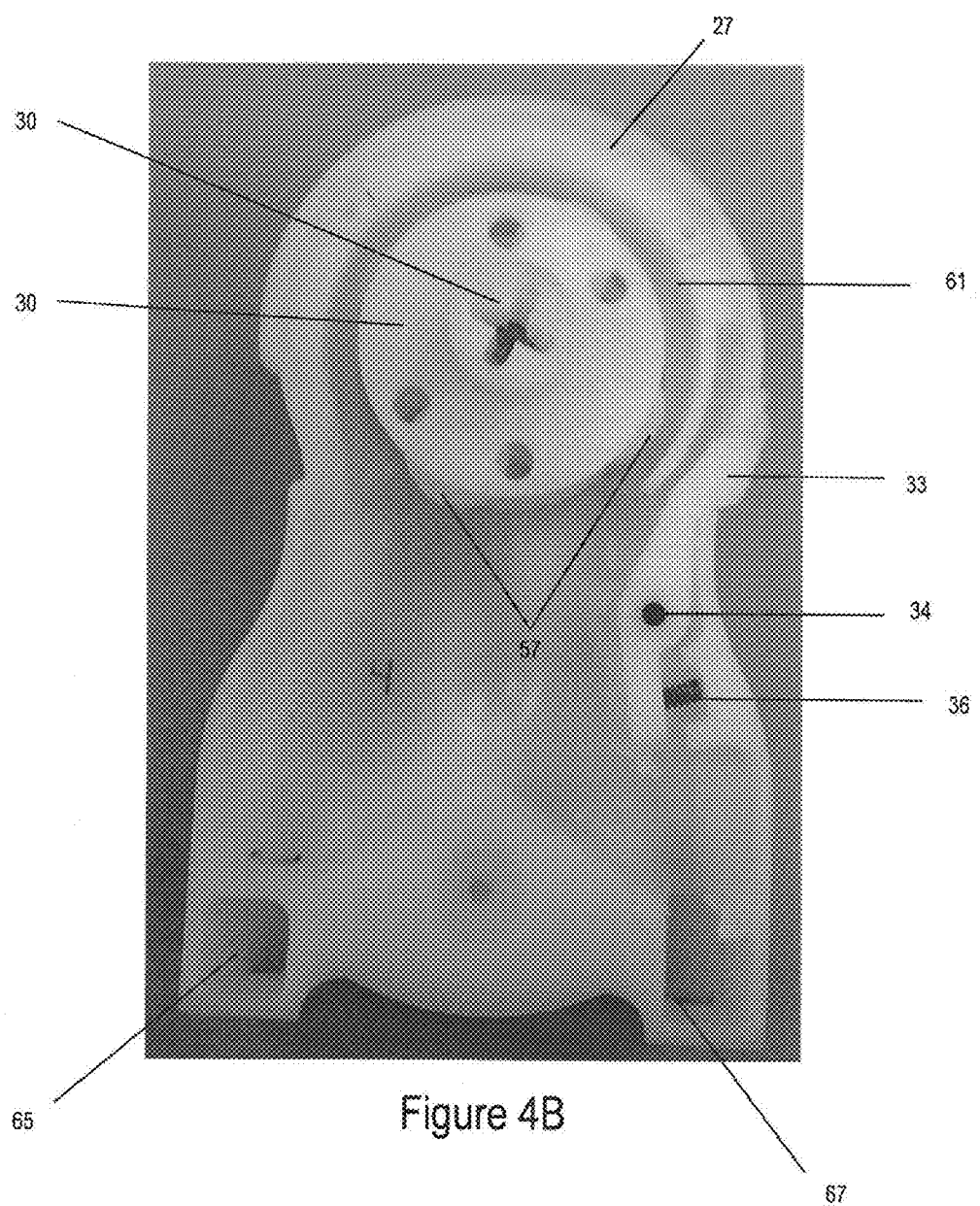
Figure 4C:
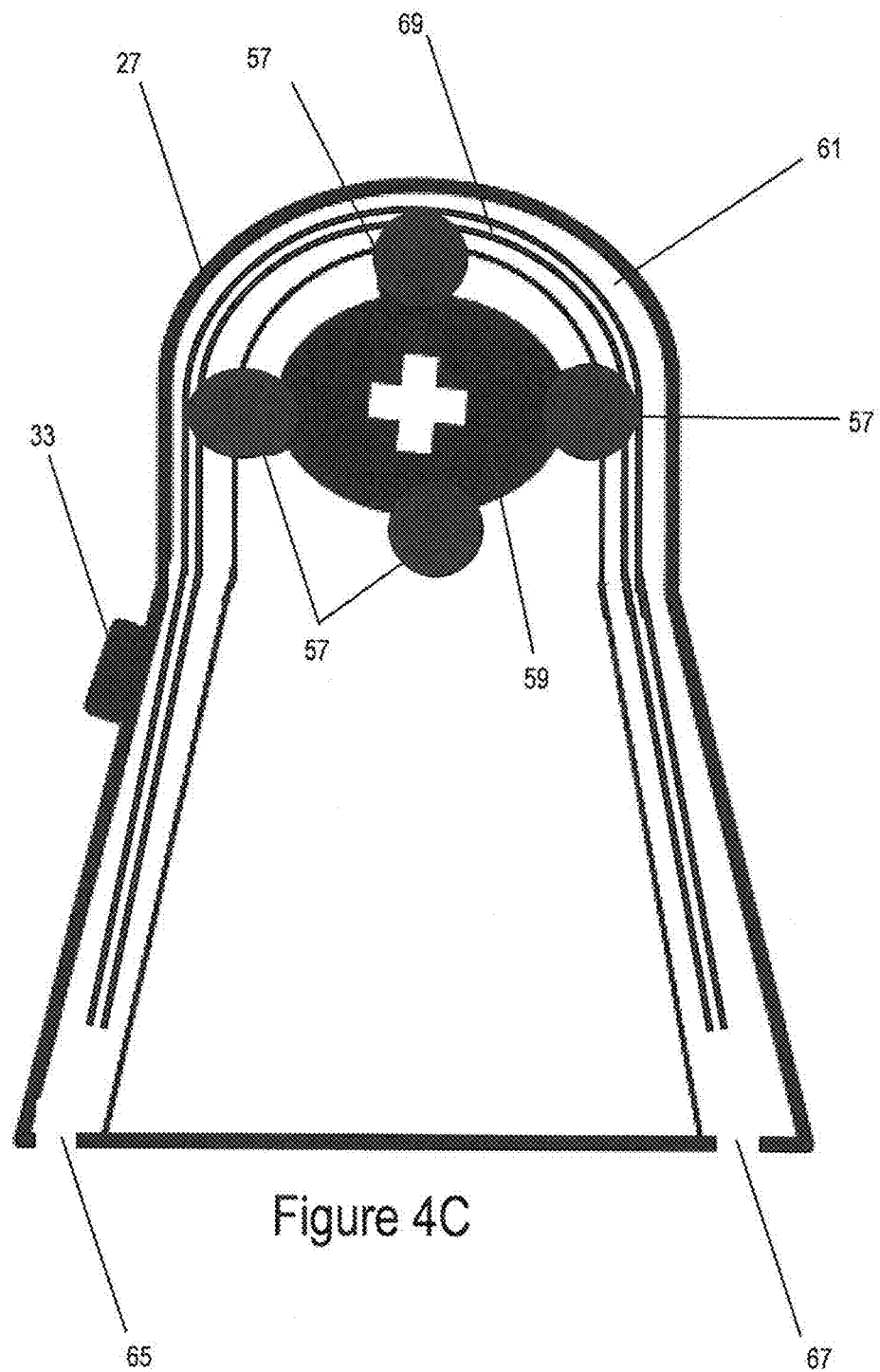

As seen in FIG. 4B-4C, the rotor 29 may be slid over the axle 63 so that the rollers 57 are aligned with the tubing track 61 to provide a clearance or space with a width of between 0.1 in-0.2 in, and in one embodiment a clearance of 0.106 in. This clearance is to provide a space for the peristaltic tubing 69 to be placed. As the drive shaft 11 rotates this causes the back plate 53 to rotate, which in turn cause the rollers 57 to move along the peristaltic tubing 69. As the rollers 57 press against and constrict the peristaltic tubing 69 this creates pressure within the tubing 69 forcing fluid to be moved at a flow rate that is dependent on rotational rate of drive shaft 11. The tubing 69 used for peristaltic pumps is well known in the art. When tubing is contacted by rollers 57 this force pinches or closes the tubing, also as known in the art for peristaltic pumps. The peristaltic tubing 69 may be placed into track 61 during the manufacturing process prior to shipment.

As seen in FIG. 4D, one end of the peristaltic pump tubing 69 may be in fluid connection with a first tube connector 73 and the other end of the tubing 69 may be in fluid connection to a second tube connector 71. The first tube connector 73 may be further connected to fluid source line 37 and the second tube connector 71 may be further connected to probe fluid line 35. The peristaltic pump tubing 69 may be connected to the fluid source line 37 and probe source line 35 inside of the pump head 27 during the manufacturing process to reduce preparation time for user and possible user errors. The pump head 27 may be shipped to the user as an accessory or component of the packaged energy delivery device to ensure the correct tubing configuration is used. This design offers several advantages over prior art device configurations. As an example, the tubing preparation and assembly steps for a 5-tine RF delivery device of the prior art require that the user manually load each tube into an occlusion bed containing five channels corresponding to the five tubing lines. Once loaded, the user must secure the occlusion bed to the pump head. The process is cumbersome and prone to user error which may result in incomplete fluid flow through all lumens. By providing pre-assembled, customized tubing attached to the disposable pump head 27, the preparation time and likelihood of error is greatly reduced.

Alternatively, the fluid line may have a tubing connector which is manually connected to probe by user providing user with options of attaching various sized probes. The type of fluid lines 37, 25, 69 being used will depend on the type of energy probe being used. For example, if the probe being used is an RF probe with dedicated fluid channels for each infusion tine, the fluid tubing set will also typically contain a dedicated lumen for each tine. For a microwave probe with a closed cooling design, fluid flows from the fluid reservoir through the pump and to the distal end of the probe. The fluid is then returned through a separate fluid channel to the fluid reservoir. To accommodate different fluid channel configurations needed for different energy delivery devices, the pump head 5 of the current invention may include tubing connectors 71 and 73 which are designed connect the single lumen tubing 69 with the device specific tubing. The reason the probe source tube 35 may be up to 5 lumens is if the ablation probe has multiple prongs each prong may have an independent fluid channel and require a dedicated fluid line. In yet another embodiment, if the ablation probe requires cooling fluid, such as a microwave probe or cooled tip RE or IRE probe, then the fluid source line 37 and probe source line 35 may both comprise of dual lumen tubing, one lumen for cooling fluid and a return lumen 75 for used cooling fluid, as seen in FIG. 4E.

Figure 4E:
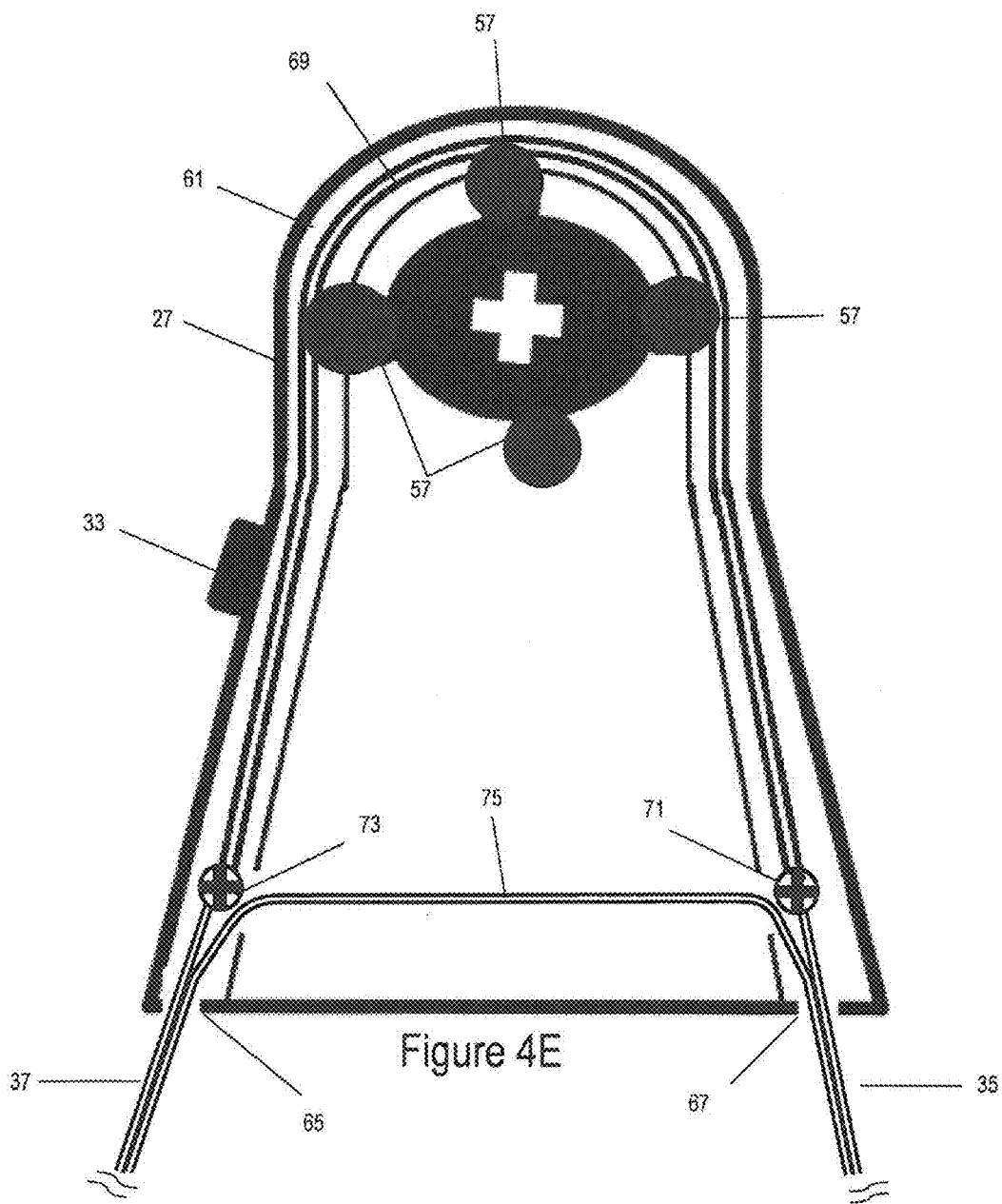

As shown in FIG. 4E, the source fluid line 37 may be in fluid communication with a cooled fluid source, such as saline, and the cooled fluid travels along the first lumen of the fluid source line 37 through the first tube connector 73, along the peristaltic pump tubing 69, through the second tube connector 71, through the first lumen of the probe source tube 35, and then flows into the cooling fluid channel of the probe (not shown). As the cooling fluid circulates and cools the ablation probe the cooling fluid begins to heat and needs to be returned to the fluid source. Pressure from pump forces the used cooling fluid to return up a second lumen of probe tubing line 35, through the return lumen 75 located inside the pump head 27, and then through a second lumen of the fluid source line 37, returning back to the fluid source to be re-cooled. The return lumen 75 is not connected to the peristaltic pump tubing and therefore is intended to be a fluid conduit between the probe source line 35 and fluid source line 37. Additionally, the disposable pump head 27 with pre-assembled, dual lumen tubing segments 37 and 35 may eliminate any tubing connection steps of prior art designs and require only a simple, single, snap fit connection of the pump head to the generator.

Figure 5:
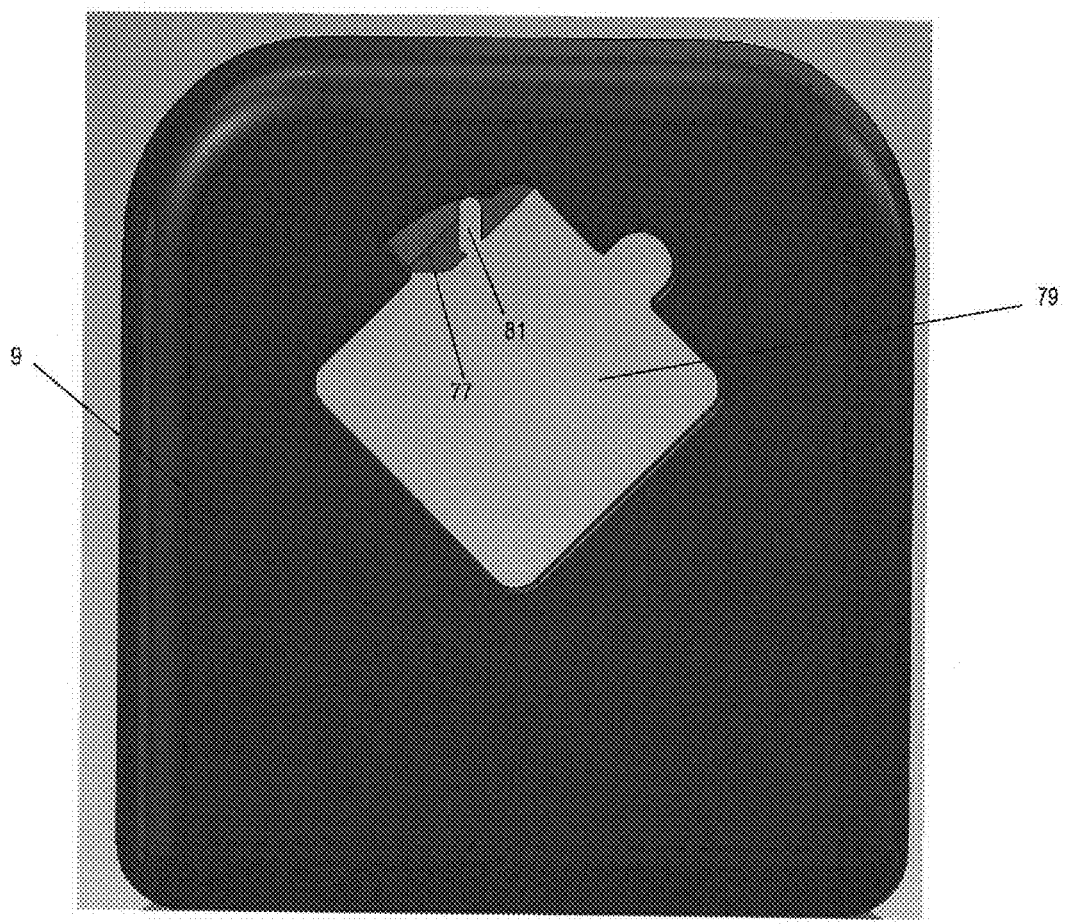
FIG. 5 is a front view of the face plate of the housing.

Referring now to FIG. 5, shown is the quick change replacement feature of the system. If the pump motor malfunctions it may need to be replaced. Since the pump motor is integrated into the energy generator replacing the pump would require the generator to be out of commission for the entire replacement time; meaning patients could not be treated during this replacement time. In order to prevent unnecessary maintenance delays the system may include a quick change replacement feature so that the pump motor may be easily removed from the housing and replaced with a new motor in a matter of minutes. The face plate 9 may comprise a motor housing port 79 which is sized so that the entire pump motor can fit through the housing port 79. Inside of the housing port 79 may be a motor securement latch 77 that may hinge when pushed or depressed. The motor securement latch 77 may comprise a slot 81 in which only a specialty tool (not shown) sold with the unit may fit. If the pump motor requires maintenance, the specialty tool may be designed to fit into the corresponding slot 81 and then by depressing or pushing latch 77 allowing the pump motor to be removed through the housing port 79. The motor may then be disconnected from the electrical connections (not shown), replaced with a new motor (not shown) which is then slid through the housing port 79 and secured into system by latch 77.

The invention claimed is:

1. A system for ablating tissue and the cooling of ablation probes, the system comprising:
   a multiple-use housing, the multiple use housing comprising:
      a first electrical connection point;
      a pump having a pump motor and a drive shaft;
      an energy generator; and
   a single-use pump head, the single-use pump head comprising:
      a rotor, the rotor having a connection point that aligns with the drive shaft of the pump;
      at least one roller attached to the rotor, the at least one roller comprising up to 6 rollers;
      a pump tubing track, the entirety of the pump tubing track being within the single-use pump head;
      a first tube connector and a second tube connector;

a second electrical connection point;

a pump tubing, the pump tubing having a first end and a second end, the first end is connected to the first tube connector and the second end is connected to the second tube connector, the pump tubing aligning with the pump tubing track, the pump tubing contained entirely within the pump head;

a fluid source line, the fluid source line having a first end and a second end, the first end is connected to an external fluid source and the second end is connected to the first tube connector;

a probe fluid line, the probe fluid line comprising a first end and a second end, the first end is connected to the second tube connector and the second end is connected to an ablation probe handle;

a return lumen, the return lumen having a first end and a second end, the first end is connected to the ablation probe handle and the second end is connected to the fluid source, the return lumen being situated within the pump head and bypassing the pump tubing track and the at least one roller attached to the rotor; and an ablation probe.

2. The system of claim 1, wherein the multiple-use housing further comprises a faceplate having at least one additional electrical connection point on the housing.

3. The system of claim 2, wherein the faceplate has a securement keyhole.

4. The system of claim 1, wherein the multiple-use housing further comprises a pump faceplate.

5. The system of claim 1, wherein the pump head further comprises a securement latch.

6. The system of claim 1, wherein the first electrical connection point aligns with and connects to the second electrical connection point when the pump head is attached to the housing.

7. The system of claim 1, the probe fluid line further comprising 5 lumens at the second end.

8. The system of claim 1, wherein the energy generator is capable of producing microwave energy.

9. The system of claim 1, wherein the energy generator is capable of producing irreversible electroporation energy.

10. The system of claim 1, wherein the energy generator is capable of producing radiofrequency energy.

\* \* \* \* \*